US012037325B2

(12) United States Patent
Matsumoto et al.

(10) Patent No.: US 12,037,325 B2
(45) Date of Patent: Jul. 16, 2024

(54) 1,2-DIAMINOBENZIMIDAZOLE DERIVATIVE

(71) Applicant: Carna Biosciences, Inc., Hyogo (JP)

(72) Inventors: Hirokazu Matsumoto, Hyogo (JP); Takao Kiyoi, Hyogo (JP); Shiori Takamatsu, Hyogo (JP); Masaaki Sawa, Hyogo (JP)

(73) Assignee: CARNA BIOSCIENCES, INC., Hyogo (JP)

( * ) Notice: Subject to any disclaimer, the term of this patent is extended or adjusted under 35 U.S.C. 154(b) by 0 days.

(21) Appl. No.: 17/870,303

(22) Filed: Jul. 21, 2022

(65) Prior Publication Data

US 2023/0097964 A1 Mar. 30, 2023

(30) Foreign Application Priority Data

Jul. 21, 2021 (JP) ................................ 2021-120698

(51) Int. Cl.
*C07D 235/30* (2006.01)
*A61K 31/437* (2006.01)
*C07D 403/12* (2006.01)
*C07D 471/04* (2006.01)

(52) U.S. Cl.
CPC ......... *C07D 403/12* (2013.01); *C07D 471/04* (2013.01); *C07B 2200/05* (2013.01)

(58) Field of Classification Search
CPC .. C07D 235/30; C07D 403/12; C07D 471/04; A61K 31/437
See application file for complete search history.

(56) References Cited

FOREIGN PATENT DOCUMENTS

WO 2017/151165 9/2017
WO 2021/193756 9/2021

OTHER PUBLICATIONS

U.S. Appl. No. 17/914,699, filed Sep. 26, 2022, entitled "Novel Benzimidazole Derivative", 155 pages, corresponding to BA above.
Paludan et al., "Immune Sensing of DNA", Immunity, 2013, vol. 38, No. 5, pp. 870-880, 11 pages.
Motwani et al., "DNA sensing by the CGAS-STING pathway in health and disease", Nature Reviews, Genetics, 2019, vol. 20, No. 11, pp. 657-674, 18 pages.
Liu et al., "Activated STING in a Vascular and Pulmonary Syndrome", The New England Journal of Medicine, 2014, vol. 371, No. 6, pp. 507-518, 12 pages.
Jeremiah et al., "Inherited STING-activating mutation underlies a familial inflammatory syndrome with lupus-like manifestations", The Journal of Clinical Investigation, 2014, vol. 124, No. 12, pp. 5516-5520, 5 pages.

MacKenzie et al., "Ribonuclease H2 mutations induce a cGAS/STING dependent innate immune response", The EMBO Journal, 2016, vol. 35, No. 8, pp. 831-844, 14 pages.
An et al., "Expression of Cyclic GMP-AMP Synthase in Patients With Systemic Lupus Erythematosus", Arthritis & Rheumatology, 2017, vol. 69, No. 4, pp. 800-807, 8 pages.
Kato et al., "Apoptosis-derived membrane vesicles drive the cGAS-STING pathway and enhance type I IFN production in systemic lupus erythematosus", Ann. Rheum. Dis., 2018, vol. 77, No. 10, pp. 1507-1515, 9 pages.
Zeng et al., "ALK is a therapeutic target for lethal sepsis", Science Translational Medicine, 2017, vol. 9, No. 412, pp. 1-15, 16 pages.
Hu et al., "STING-medicated intestinal barrier dysfunction contributes to lethal sepsis", EBioMedicine, 2019, vol. 41, pp. 497-508, 12 pages.
Yu et al., "STING-medicated inflammation in Kupffer cells contributes to progression of nonalcoholic steatohepatitis", The Journal of Clinical Investigation, 2019, vol. 129, No. 2, pp. 546-555, 10 pages.
Iracheta-Vellve et al., "Endoplasmic Reticulum Stress-induced Hepatocellular Death Pathways Mediate Liver Injury and Fibrosis via Stimulator of Interferon Genes", The Journal of Biological Chemistry, 2016, vol. 291, No. 52, pp. 26794-26805, 13 pages.
Maekawa et al., "Mitochondrial Damage Causes Inflammation via cGAS-STING Signaling in Acute Kidney Injury", Cell Reports, 2019, vol. 29, No. 5, pp. 1261-1273.e1-e6, 19 pages.
Ahn et al., "STING manifests self DNA-dependent inflammatory disease", PNAS, 2012, vol. 109, No. 47, pp. 19386-19391, 6 pages.
Ablasser et al., "cGAS in action: Expanding roles in immunity and inflammation", Science, 2019, vol. 363, No. 10455, pp. 1-9, 11 pages.
Sliter et al., "Parkin and PINK1 mitigate STING-induced inflammation", Nature, 2018, vol. 561, No. 7722, pp. 258-262, 16 pages.
Skopelja-Gardner, et al., "Role of the cGAS-STING pathway in systemic and organ-specific diseases", Nature, 2022, vol. 18, pp. 558-572, 15 pages.
Ramanjulu et al., "Design of amidobenzimidazole STING receptor agonists with systemic activity", Nature, 2018, vol. 564, vol. 7736, pp. 439-443, 16 pages.
International Search Report issued Dec. 16, 2022 in International Application No. PCT/IB2022/000396, 4 pages.

(Continued)

*Primary Examiner* — Bruck Kifle
(74) *Attorney, Agent, or Firm* — Wenderoth, Lind & Ponack, L.L.P.

(57) ABSTRACT

Provided herein are novel compounds having an inhibitory effect on the activation of a STING pathway. The provided compounds are 1,2-diaminobenzimidazole derivatives represented by a compound formula (I) or a pharmaceutically acceptable salt thereof:

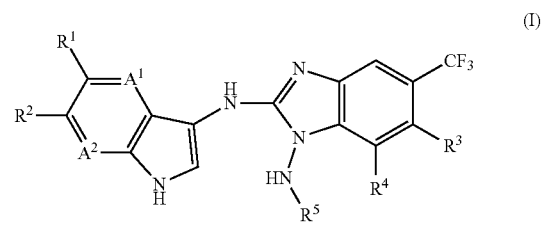

wherein $A^1$, $A^2$, $R^1$, $R^2$, $R^3$, $R^4$, and $R^5$ are defined in the specification.

17 Claims, 2 Drawing Sheets

(56) References Cited

OTHER PUBLICATIONS

International Preliminary Report on Patentability issued Jan. 18, 2024 in International Application No. PCT/IB2022/000396, 8 pages.
Xi et al., "Design, Synthesis, and Biological Evaluation of Amidobenzimidazole Derivatives as Stimulator of Interferon Genes (STING) Receptor Agonists", Journal of Medical Chemistry, 2020, vol. 63, pp. 260-282, 23 pages.
Registry (STN), Apr. 19, 2016, CAS Registry No. 1892646-11-5, 1 page.
Registry (STN), Apr. 24, 2016, CAS Registry No. 1896125-09-9, 1 page.
Registry (STN), Apr. 24, 2016, CAS Registry No. 1896125-31-7, 1 page.

1,2-DIAMINOBENZIMIDAZOLE DERIVATIVE

CROSS-REFERENCE TO RELATED APPLICATIONS

This application claims the benefit of priority to Japanese Appl. No. 2021-120698, filed Jul. 21, 2021, the entirety of which is herein incorporated by reference.

TECHNICAL FIELD OF THE INVENTION

The present invention relates to a medicament, and particularly to a novel 1,2-diaminobenzimidazole derivative having an inhibitory effect on activation of a STING pathway or a pharmaceutically acceptable salt thereof.

BACKGROUND OF THE INVENTION

STING (STimulator of INterferon Genes) plays an important role in biological defense mechanisms as a molecule that induces innate immune responses to various RNA and DNA viral infections, or the like. The STING binds to ligands such as cyclic GMP-AMP (cGAMP), a cyclic dinucleotide generated by cyclic GMP-AMP synthetase (cGAS), to activate TANK-binding kinase 1 (TBK1) and induces type-I IFN production via transcription factor IRF3 (Non Patent Literature 1).

Recently, it has been reported that STING is activated even by tumor-derived self-DNA and mitochondria) DNA, or the like, and induces proinflammatory responses, attracting increased attention as a drug target for cancer and autoimmune diseases (Non Patent Literature 2).

Human STING is encoded by a gene, Tmem173, and an autoinflammatory disease called STING-associated vasculopathy with onset in infancy (SAVI) has been reported as a genetic disease caused by mutations in the Tmem173. SAVI patients have mutations that makes the STING constitutively active, and excessive inflammation causes abnormal antibody production and tissue damage in the skin and lungs (Non Patent Literature 3). It has also been reported that even patients with familial chilblain lupus and familial lupus-like syndrome, which are autoinflammatory genetic diseases, have activating mutations in the STING (Non Patent Literature 4).

In addition, it is known that accumulation of self-DNA in cells due to insufficient DNA degradation results in constitutive activation of a STING pathway, causing autoimmune diseases. Aicardi-Goutières syndrome (AGS) is considered one of such diseases, and it has been reported that deficiency of STING in a model mouse for this disease suppresses the symptoms (Non Patent Literature 5).

In systemic lupus erythematosus (SLE), nucleic antibodies, which are autoantibodies, and particularly anti-DNA antibodies are excessively produced, being considered to be the cause of the excessive immune responses. In recent year, however, it has been revealed that activation of the STING pathway induces interferon production important in pathological conditions of SLE. In other words, cGAMP contained in patient peripheral blood is correlated with pathological scores, and it has also been reported that interferon induction by cGAMP in patient serum is suppressed in STING-deficient cells (Non Patent Literatures 6 and 7).

Since the STING is involved in various immune responses in vivo, it has also been reported that the STING is involved in many diseases. For example, in the study of sepsis in which systematic inflammation caused by a pathogen infection leads to organ damage, it has been reported that the deficiency of the STING in a septic model mouse alleviates the symptoms (Non Patent Literatures 8 and 9). In addition, the involvement of STING in inflammatory diseases such as non-alcoholic steatohepatitis (NASH), hepatic fibrosis, acute pancreatitis, and polyarthritis has been revealed by investigations using model mice (Non Patent Literatures 10, 11, 12, and 13). Furthermore, it has been revealed that in patients with Parkinson's disease, a neurodegenerative disease, inflammatory cytokines are increased due to disruption of mitochondrial homeostasis, while it has been reported that the deficiency of the STING in model mice ameliorates these abnormalities (Non Patent Literatures 14 and 15).

Therefore, activation inhibitors of STING pathways are useful in the treatment of various inflammatory and immune diseases in which the STING pathways are involved.

SUMMARY OF THE INVENTION

An object of the present invention is to provide a medicament and particularly a novel 1,2-diaminobenzimidazole derivative having an inhibitory effect on activation of a STING pathway (e.g., by inhibiting STING or cGAS) or a pharmaceutically acceptable salt thereof.

The present invention is achieved by the following (1) to (6):

(1) A 1,2-diaminobenzimidazole derivative represented by the following formula (I) or a pharmaceutically acceptable salt thereof:

Chemical Formula 1

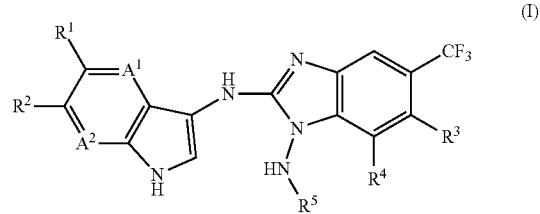

wherein $A^1$ represents a nitrogen atom or $C-R^6$, $A^2$ represents a nitrogen atom or $C-R^7$, $R^1$ represents a halogen atom or an alkyl group, each of $R^2$, $R^3$, $R^4$, $R^6$ and $R^7$ independently represents a hydrogen atom or a fluorine atom, and $R^5$ represents a hydrogen atom or an optionally substituted alkyl group.

(2) The 1,2-diaminobenzimidazole derivative of the formula (I) according to (1) or a pharmaceutically acceptable salt thereof, wherein $A^1$ and $A^2$ are represented by $C-R^6$ and $C-R^7$ respectively.

(3) The 1,2-diaminobenzimidazole derivative of the formula (I) according to (1) or a pharmaceutically acceptable salt thereof, wherein $A^1$ and $A^2$ are represented by a nitrogen atom and $C-R^7$ respectively.

(4) The 1,2-diaminobenzimidazole derivative of the formula (I) according to (1) or a pharmaceutically acceptable salt thereof, wherein $A^1$ and $A^2$ are represented by $C-R^6$ and a nitrogen atom respectively.

(5) The 1,2-diaminobenzimidazole derivative of the formula (I) according to (1) or (2), or a pharmaceutically acceptable salt thereof, wherein R' is represented by a halogen atom.

(6) A compound of Examples 1 to 29 described later, or a pharmaceutically acceptable salt thereof.

As a result of various investigations to solve the above-mentioned problem, the present inventors have found that novel 1,2-diaminobenzimidazole derivatives represented by the formula (I) or pharmaceutically acceptable salts thereof exhibit an excellent inhibitory effect on activation of the STING pathway and completed the present invention. The compounds provided by the present invention are useful as a preventive or therapeutic pharmaceutical (pharmaceutical composition) for diseases known to be associated with STING-mediated cellular responses, such as inflammatory diseases, autoimmune diseases, or cancer. When combined with therapeutic agents for other inflammatory diseases, autoimmune diseases, and cancer, the compounds are expected to have an effect on immune responses and thus are also useful as a therapeutic pharmaceutical (pharmaceutical composition). As a STING inhibitor, they are further useful as a reagent for experiments and research.

DETAILED DESCRIPTION OF CERTAIN EMBODIMENTS

Figure 1:
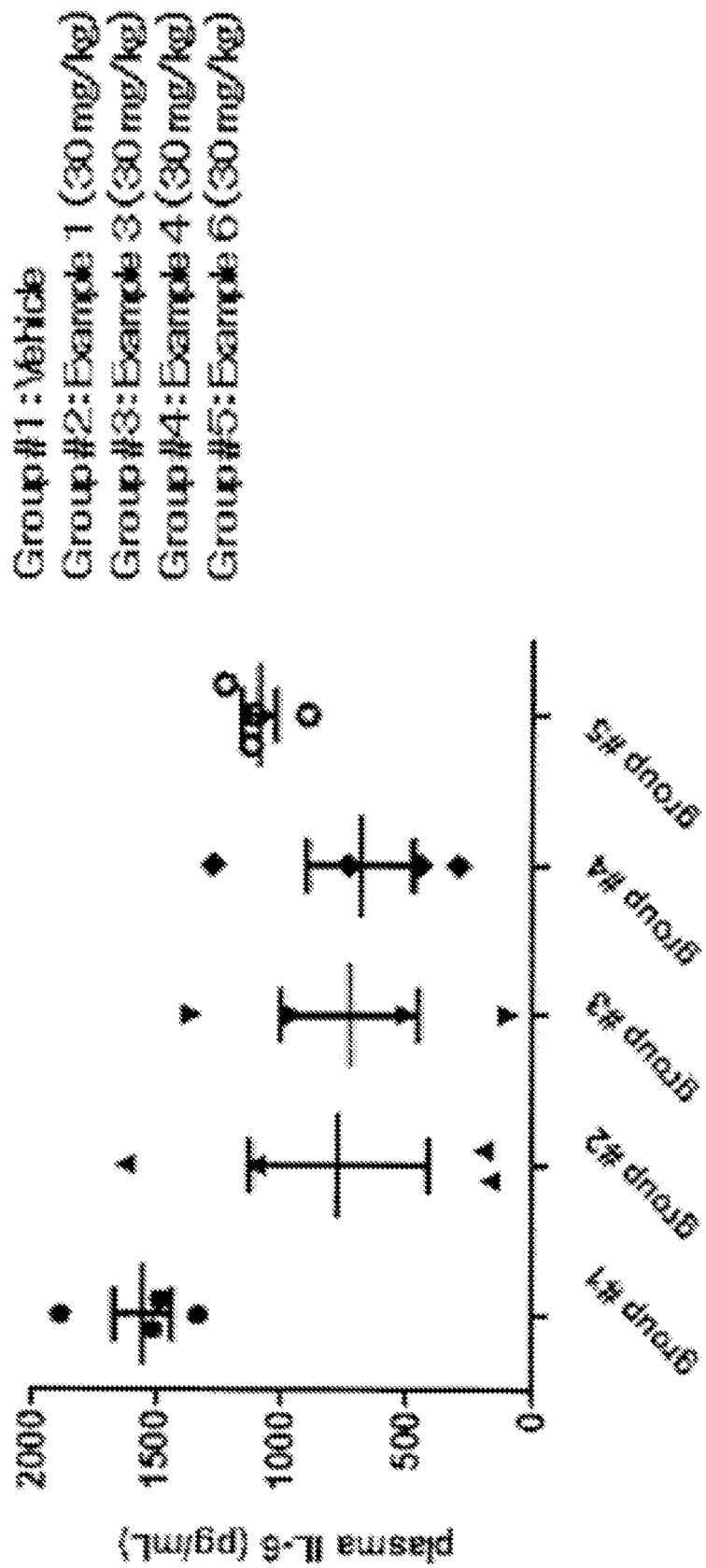
FIG. 1 shows a suppressing effect of a representative compound of Example on IL-6 production for STING agonist-stimulated mouse models (Test Example 3).

1. General Description of Certain Embodiments of the Invention

Hereinafter, the present invention is described in detail. The novel 1,2-diaminobenzimidazole derivative of the present invention is represented by the following formula (I):

Chemical Formula 2

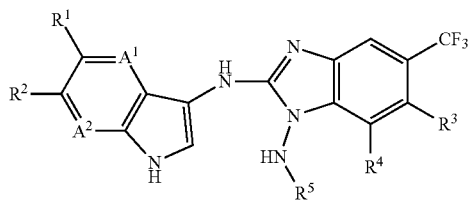

(I)

and is a compound having a basic structure in which a bicyclic nitrogen-containing heteroaryl ring is substituted with a 2-amino group of the 1,2-diaminobenzimidazole ring.

More specifically, in the formula (I), $A^1$ represents a nitrogen atom or $C-R^6$; $A^2$ represents a nitrogen atom or $C-R^7$; $R^1$ represents a halogen atom or an alkyl group; $R^2$, $R^3$, $R^4$, $R^6$, and $R^7$ each independently represent a hydrogen atom or a fluorine atom; and $R^5$ represents a hydrogen atom or an optionally substituted alkyl group.

One aspect of the 1,2-diaminobenzimidazole derivatives of the present invention includes a 1,2-diaminobenzimidazole derivative or a pharmaceutically acceptable salt thereof, wherein in formula (I), $A^1$ and $A^2$ are each represented by $C-R^6$ and $C-R^7$.

One aspect of the 1,2-diaminobenzimidazole derivatives of the present invention includes a 1,2-diaminobenzimidazole derivative or a pharmaceutically acceptable salt thereof, wherein in formula (I), $A^1$ is represented by a nitrogen atom; and $A^2$ is represented by $C-R^7$.

One aspect of the 1,2-diaminobenzimidazole derivatives of the present invention includes a 1,2-diaminobenzimidazole derivative or a pharmaceutically acceptable salt thereof, wherein in formula (I), $A^1$ is represented by $C-R^6$; and $A^2$ is represented by a nitrogen atom.

One aspect of the 1,2-diaminobenzimidazole derivatives of the present invention includes a 1,2-diaminobenzimidazole derivative or a pharmaceutically acceptable salt thereof, wherein in formula (I), $A^1$ and $A^2$ are each represented by $C-R^6$ and $C-R^7$; and $R^1$ is represented by a halogen atom.

One aspect of the 1,2-diaminobenzimidazole derivatives of the present invention includes in formula (I) a compound described later in Examples 1 to 29 and a pharmaceutically acceptable salt thereof.

In another aspect, the novel 1,2-diaminobenzimidazole derivative of the present invention is represented by the following formula (I-a):

Chemical Formula 2.1

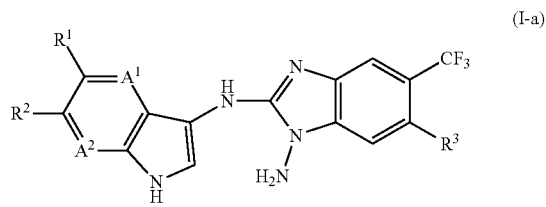

(I-a)

or a pharmaceutically acceptable salt thereof, wherein $A^1$ represents a nitrogen atom or $C-R^6$; $A^2$ represents a nitrogen atom or $C-R^7$; $R^1$ represents a halogen atom or an alkyl group; and each of $R^2$, $R^3$, $R^6$ and $R^7$ independently represents a hydrogen atom or a fluorine atom.

One aspect of the 1,2-diaminobenzimidazole derivatives of the present invention includes a 1,2-diaminobenzimidazole derivative or a pharmaceutically acceptable salt thereof, wherein in formula (I-a), $A^1$ and $A^2$ are each represented by $C-R^6$ and $C-R^7$.

One aspect of the 1,2-diaminobenzimidazole derivatives of the present invention includes a 1,2-diaminobenzimidazole derivative or a pharmaceutically acceptable salt thereof, wherein in formula (I-a), $A^1$ is represented by a nitrogen atom; and $A^2$ is represented by $C-R^7$.

One aspect of the 1,2-diaminobenzimidazole derivatives of the present invention includes a 1,2-diaminobenzimidazole derivative or a pharmaceutically acceptable salt thereof, wherein in formula (I-a), $A^1$ is represented by $C-R^6$; and $A^2$ is represented by a nitrogen atom.

One aspect of the 1,2-diaminobenzimidazole derivatives of the present invention includes a 1,2-diaminobenzimidazole derivative or a pharmaceutically acceptable salt thereof, wherein in formula (I-a), $A^1$ and $A^2$ are each represented by $C-R^6$ and $C-R^7$; and $R^1$ is represented by a halogen atom.

One aspect of the 1,2-diaminobenzimidazole derivatives of the present invention includes a 1,2-diaminobenzimidazole derivative or a pharmaceutically acceptable salt thereof, wherein in formula (I-a), $A^1$ and $A^2$ are each represented by $C-R^6$ and $C-R^7$; and $R^6$ and $R^7$ are each represented by hydrogen.

One aspect of the 1,2-diaminobenzimidazole derivatives of the present invention includes a 1,2-diaminobenzimidazole derivative or a pharmaceutically acceptable salt thereof, wherein in formula (I-a), $A^1$ and $A^2$ are each represented by C—R⁶ and C—R⁷; R⁶ and R⁷ are each represented by hydrogen; and R¹ is represented by a halogen atom.

One aspect of the 1,2-diaminobenzimidazole derivatives of the present invention includes a 1,2-diaminobenzimidazole derivative or a pharmaceutically acceptable salt thereof, wherein in formula (I-a), A¹ and A² are each represented by C—R⁶ and C—R⁷; R², R⁶ and R⁷ are each represented by hydrogen; and R¹ is represented by a halogen atom.

One aspect of the 1,2-diaminobenzimidazole derivatives of the present invention includes a 1,2-diaminobenzimidazole derivative or a pharmaceutically acceptable salt thereof, wherein in formula (I-a), A¹ and A² are each represented by C—R⁶ and C—R⁷; R³, R⁶ and R⁷ are each represented by hydrogen; and R¹ is represented by a halogen atom.

One aspect of the 1,2-diaminobenzimidazole derivatives of the present invention includes a 1,2-diaminobenzimidazole derivative or a pharmaceutically acceptable salt thereof, wherein in formula (I-a), A¹ and A² are each represented by C—R⁶ and C—R⁷; R², R³, R⁶ and R⁷ are each represented by hydrogen; and R¹ is represented by a halogen atom.

The terms used in the present specification are described below.

2. Compounds and Definitions

A reference to a compound (e.g., 1,2-diaminobenzimidazole derivative) of formula (I) includes reference to any subgenus and/or species set forth herein, including reference to a compound of formula (I-a).

The "halogen atom" represents, unless otherwise specified, a fluorine atom, a chlorine atom, a bromine atom, or an iodine atom.

The alkyl group means, unless otherwise described, a linear or branched saturated hydrocarbon group with 1 to 4 carbon atoms ($C_{1-4}$ alkyl), and specific examples thereof include methyl, ethyl, propyl, isopropyl, n-butyl, isobutyl, sec-butyl, and tert-butyl, etc.

The substituents for the terms are then described.

Examples of substituents for alkyl groups that may be substituted include halogen atoms, and one or a plurality of the same or different halogen atoms may be substituted at any positions.

Examples of other substituents for alkyl groups that may be substituted include hydroxyl groups, methoxy groups, dimethylamino groups, cyclopropyl groups, dimethylcarbamoyl groups, cyano groups, and morphonyl groups, etc and one or a plurality of the same or different substituents, including the hydrogen atoms, may be substituted at any positions of alkyl groups.

A compound of formula (I) of the present invention may have isomers, for example, depending on the types of substituents. Although chemical structures of only one form of those isomers may be described herein, and the present invention contains not only all isomers (geometrical isomers, optical isomers, tautomers, etc.) that may be generated because of the structures, but also isomers alone or mixtures thereof.

In the present invention, the "hydrogen atom" includes ¹H and ²H (D), and includes not only a deuterium converter in which any one or more of IH in compounds represented by formula (I) are converted to ²H(D) but also the compounds represented by formula (I). For example, in the case of a compound having a methyl group —CH₃, a compound having a —CD₃ group, a —CD₂H group, or a —CDH₂ group is also included.

The pharmaceutically acceptable salts of a compound of formula (I) of the present invention include inorganic acid salts with hydrochloric acid, sulfuric acid, carbonic acid, phosphoric acid, or the like; and organic acid salts with formic acid, acetic acid, fumaric acid, maleic acid, methanesulfonic acid, p-toluenesulfonic acid, or the like. In addition to alkali metal salts with sodium, potassium, or the like; alkaline earth metal salts with magnesium, calcium, or the like; organic amine salts with lower alkyl amine, lower alcohol amine, or the like; and basic amino acid salts with lysine, arginine, ornithine, or the like, ammonium salts or the like are also included in the present invention.

A compound of formula (I) of the present invention or a pharmaceutically acceptable salt thereof include both the intermolecular salts and solvates such as their hydrates.

A compound of formula (I) of the present invention or a pharmaceutically acceptable salt thereof can be produced, for example, by the following methods. Note that in the production methods shown below, if the defined groups change under the conditions of methods carried out or are unsuitable for carrying out the methods, the methods normally used in organic synthetic chemistry, such as protection and deprotection of functional groups (T. W. Greene, Protective Groups in Organic Synthesis 3rd Edition, John Wiley & Sons, Inc., 1999) are implemented, thereby making it possible to produce them more easily. The order of the reaction steps such as substituent introduction can be changed if necessary.

The synthesis of the 1,2-diaminobenzimidazole derivative disclosed in the present invention is described in detail below using general reaction schemes. The compounds of the present invention of formula (I) disclosed herein can be produced by methods described in schemes 1 to 7 below. As listed in Examples, the compounds can be produced by the general synthetic methods and a starting material of commercial products or a starting material synthesized from commercial compounds by known methods or methods similar thereto, or by varying methods well known to those skilled in the art.

Each of variable moieties shown in the following schemes is applied to all functional groups detailed in compounds provided in the present invention. Tautomers and solvates (e.g., hydrates) of the compounds of formula (I) are also included in the present invention.

The meanings of abbreviations and symbols used in the following description are as follows.
EDCI-HCl: 1-ethyl-3-(3-dimethylaminopropyl)carbodiimide hydrochloride
DMF: N,N-dimethylformamide
THF: tetrahydrofuran
NMP: N-methylpyrrolidone
DIPEA: N,N-diisopropylethylamine
Boc₂O: di-tert-butyl dicarbonate
Boc: tert-butoxycarbonyl

3. Methods of Producing Compounds of the Present Invention

A compound represented by formula (I) of the present invention can be produced, for example, by Scheme 1.

Scheme 1.

Chemical Formula 3

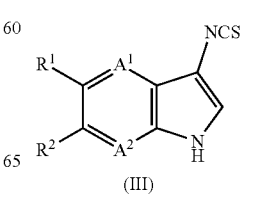

(III)

+

-continued

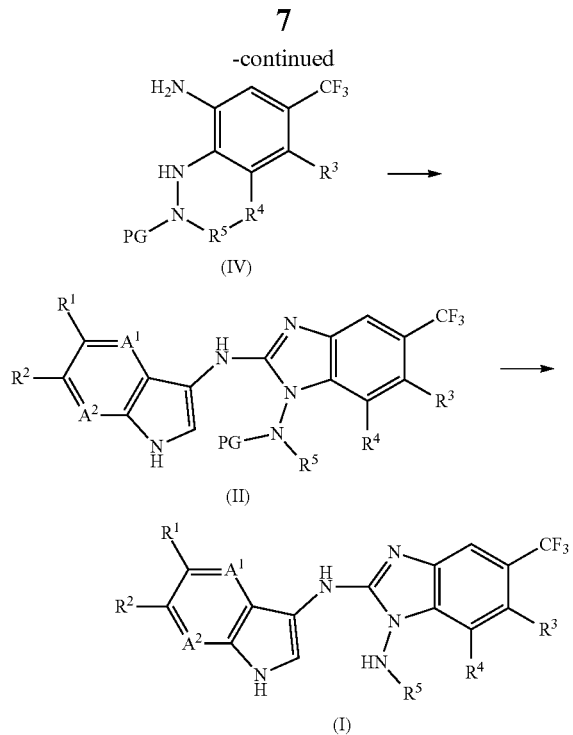

wherein $A^1$, $A^2$, $R^1$, $R^2$, $R^3$, $R^4$ and $R^5$ each have the same meaning as defined above, and PG represents a protecting group.

A compound of formula (I) of the present invention can be produced by deprotecting compound (II) obtained by cyclizing thiourea obtained by coupling reaction of isothiocyanate (III) and aniline (IV). In other words, the corresponding thiourea can be obtained by reacting the isothiocyanate (III) with 0.5 to 1.5 molar equivalents of aniline (IV) in a solvent.

Any solvent inert to the reaction may be used, such as chloroform, THF, DMF, and NMP, and DMF can be preferably used. The reaction can be carried out in a range of 0° C. to 100° C. for several minutes to several days, and preferably carried out at room temperature to 80° C. for 10 minutes to 24 hours. The reaction may give mixtures of thiourea reacted with NH2 of aniline and thiourea reacted with NH of hydrazine, and these mixtures can be used for the next reaction without purification, but may be purified. The resulting thiourea is then subjected to cyclization reaction in a solvent under condensation conditions commonly used in organic synthetic chemistry, for example, using a condensing agent such as 1 to 3 molar equivalents of EDCI-HCl to obtain compound (II).

Any solvent inert to the reaction may be used and is not particularly limited. For example, DMF, THF, and NMP may be used, and DMF can be preferably used. The reaction can be carried out in a range of 0° C. to 100° C. for several minutes to several days, and preferably carried out under room temperature to 80° C. for 0.5 hours to 24 hours. A compound of formula (I) of the present invention can be obtained by removing a protecting group PG of the resulting composition (II) via deprotection under conditions commonly used in organic chemistry.

The isothiocyanate (III) used as a raw material for Scheme 1 can be produced from compounds (V), for example as shown in Scheme 2.

Scheme 2.

Chemical Formula 4

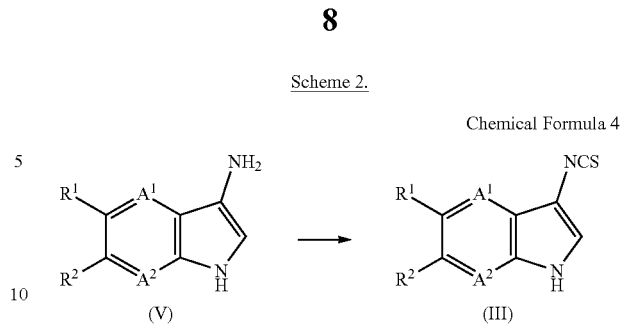

wherein, $A^1$, $A^2$, $R^1$ and $R^2$ each have the same meaning as defined above.

The isothiocyanate (III) can be produced by converting an amino group of the compound (V) to an isothiocyanate group. In other words, the isothiocyanate (III) can be obtained by reacting the compound (V) with 1 to 3 molar equivalents of an isothiocyanated reagent such as thiophosgene in the presence of a base such as 1 to 3 molar equivalents of DIPEA in a solvent. Any solvent inert to the reaction can be used, such as chloroform or THF, and THF can be preferably used. The reaction can be carried out in the range of −20° C. to 50° C. for several minutes to several days, and preferably carried out at 0° C. to room temperature for 10 minutes to 24 hours.

The compound (V) used as a raw material for Scheme 2 can be produced from compound (VI), for example, as shown in Scheme 3.

Scheme 3.

Chemical Formula 5

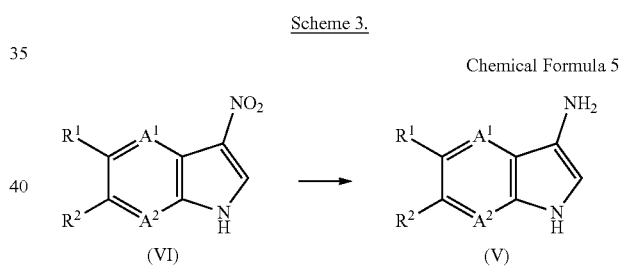

wherein $A^1$, $A^2$, $R^1$ and $R^2$ each have the same meaning as defined above.

The compound (V) can be produced by reducing a nitro group of the compound (VI). In other words, the compound (V) can be obtained by reducing the nitro group of the compound (VI) in a solvent by a reduction method normally used in organic synthetic chemistry, such as catalytic reduction using palladium carbon or the like, and metal reduction using tin, zinc, iron, or the like.

In the reduction reaction, an amino group of the compound (V) goes through a compound protected by a Boc group for the purpose of improving the yield. In other words, the compound in which the amino group of the compound (V) is protected by the Boc group by reacting the compound (VI) with Boc$_2$O in the presence of metals such as ammonium chloride and zinc in a solvent. The Boc group can be removed via deprotection under conditions commonly used in organic chemistry such as using hydrochloric acid.

The compound (VI) used as a raw material for Scheme 3 can be obtained commercially or produced from compound (VII), for examples, as shown in Scheme 4.

Scheme 4.

Chemical Formula 6

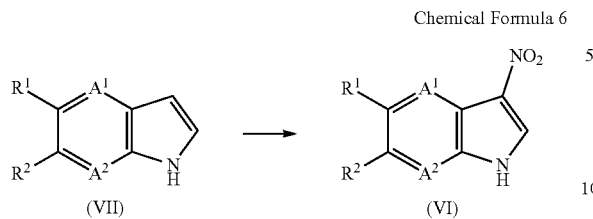

wherein $A^1$, $A^2$, $R^1$ and $R^2$ each have the same meaning as defined above.

The compound (VI) can be produced by nitration of the compound (VII). In other words, the compound (VI) can be obtained by reacting the compound (VII) with nitration reaction conditions commonly used in organic chemistry, such as fuming nitric acid or mixed acid of concentrated sulfuric acid and nitric acid. The nitrating agent is not particularly limited, and for example, 1 to 5 molar equivalents of potassium nitrate can be used in the presence of concentrated sulfuric acid. The reaction can be carried out in a range of −20° C. to 50° C. for several minutes to several days, and preferably carried out at 0° C. to room temperature for 10 minutes to 1 hour.

The compound (VI) can also be produced by known methods (e.g., see Bioorg. Med. Chem. 2007, 15, 3248-3265 or Tetrahedron Letters 2012, 53, 4841-4842) or methods similar thereto. In other words, the compound (VI) is obtained by reacting the compound (VII) with 1 to 5 molar equivalents of a nitrating agent and 1 to 5 molar equivalents of acid chloride in a solvent. Any solvent inert to the reaction can be used and is not particularly limited. For example, acetonitrile can be used as the reaction solvent, 1 to 5 molar equivalents of silver nitrate can be used as the nitrating agent, and 1 to 5 molar equivalents of benzoyl chloride can be used as the acid chloride. The reaction can be carried out in a range of −10° C. to 50° C. for several minutes to several days, and preferably carried out under 0° C. to room temperature for 1 hour to 24 hours.

The compound (VII) used as a raw material for Scheme 4 can be obtained commercially or produced by known methods or methods similar thereto.

The compound (V) used as a raw material for Scheme 2 can also be produced, for example, by Scheme 5.

Scheme 5.

Chemical Formula 7

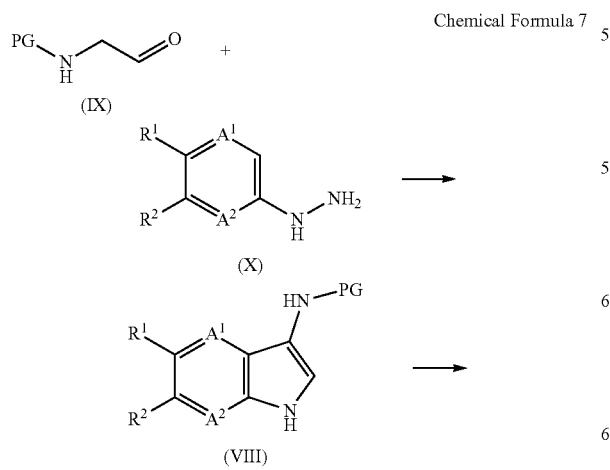

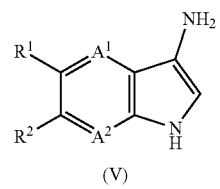

wherein $A^1$, $A^2$, $R^1$ and $R^2$ each have the same meaning as defined above, and PG represents a protecting group.

The compound (V) can be produced by deprotecting the compound (VIII) obtained by Fischer indole synthesis using compound (IX) and compound (X). In other words, the compound (IX) is reacted with 0.5 to 1.5 molar equivalents of the compound (X) in a solvent under the conditions of Fischer indole synthesis to obtain the compound (VIII). Any solvent inert to the reaction can be used, such as chloroform, 1,2-dichloroethane, THF, and toluene, and a mixed solvent of 1,2-dichloroethane/toluene can be preferably used.

The reaction can be carried out in a range of 0° C. to 100° C. for several minutes to several days, and preferably carried out at room temperature to 100° C. for 30 minutes to 24 hours. The compound (V) can be obtained by treating the protecting group of the resulting compound (VIII) under deprotection conditions commonly used in synthetic organic chemistry.

The compounds (IX) and compounds (X) used as raw materials for Scheme 5 can be obtained commercially or produced by known methods or methods similar thereto.

The aniline (W) used as a raw material for Scheme 1 can be produced from compound (XI), for example, as shown in Scheme 6.

Scheme 6.

Chemical Formula 8

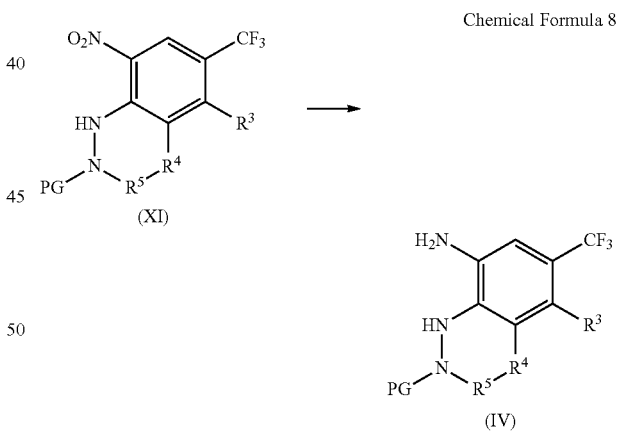

wherein $R^3$, $R^4$ and $R^5$ each have the same meaning as defined above, and PG represents a protecting group.

The aniline (IV) can be produced by reducing a nitro group of the compound (XI). In other words, the aniline (IV) can be obtained by reducing the nitro group of the compound (XI) in a solvent by the reduction methods normally used in organic synthetic chemistry, such as catalytic reduction using palladium carbon, metal reduction using tin, zinc, iron, or the like.

The compound (XI) used as a raw material for Scheme 6 can be produced, for example, by a method represented in Scheme 7.

Scheme 7.

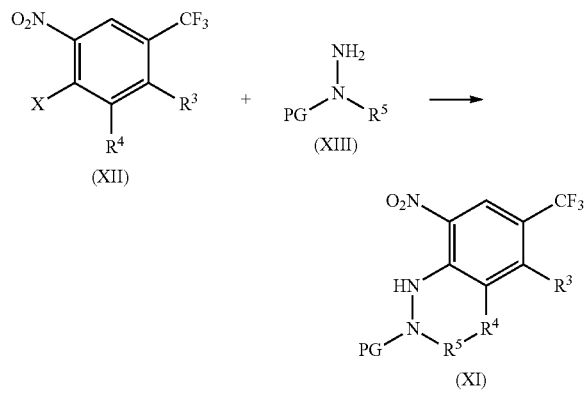

wherein R³, R⁴ and R⁵ each have the meaning as defined above, X represents a halogen atom, and PG represents a protecting group.

The compound (XI) can be produced by a nucleophilic substitution reaction using compound (XII) and compound (XIII). In other words, the compound (XI) can be obtained by reacting the compound (XII) with 0.5 to 2 molar equivalents of compound (XIII) in a solvent. Any solvent inert to the reaction can be used and is not particularly limited, but NMP can be preferably used. The reaction can be carried out in a range of 0° C. to 180° C. for several minutes to several days, and preferably carried out under room temperature to 120° C. for 30 minutes to 24 hours.

In addition, the compound (XII) and the compound (XIII) used as raw materials for Scheme 7 can be obtained commercially or produced by known methods or methods similar thereto.

The above methods can be combined as appropriate, and the methods normally used in organic synthetic chemistry (e.g., nucleophilic substitution reaction of amino groups, alkylation reaction of amino groups, Mitsunobu reaction, conversion reaction of carboxyl groups to substituted or unsubstituted carboxamide groups, cross-coupling reaction such as Suzuki-Miyaura reaction, and reduction of carbon-carbon double bond by hydrogenation reaction) can be carried out to obtain a compound of formula (I) of the present invention having the desired functional group at the desired position.

4. Uses of Compounds of the Present Invention

A compound of formula (I) of the present invention or a pharmaceutically acceptable salts thereof can be prepared in the form of conventional pharmaceutical formulations (pharmaceutical compositions) suitable for oral, parenteral, or topical administration.

Formulations for oral administration include solid formulations such as tablets, granules, powders, and capsules, and liquid formulations such as syrups. The formulations can be prepared by conventional methods. Solid dosage forms can be prepared by using conventional pharmaceutical carriers such as lactose, starch such as cornstarch, crystalline cellulose such as microcrystalline cellulose, hydroxypropyl cellulose, calcium carboxymethyl cellulose, talc, and magnesium stearate. The capsules can be prepared by encapsulating the granules or powder prepared in this way. The syrups can be prepared by dissolving or suspending a compound of formula (I) of the present invention or a pharmaceutically acceptable salt thereof in an aqueous solution containing sucrose, carboxymethyl cellulose, and the like.

Formulations for parenteral administration include injections such as intravenous infusions. Infusion formulations can also be prepared by conventional methods and can be incorporated as appropriate in isotonic agents (e.g., mannitol, sodium chloride, glucose, sorbitol, glycerol, xylitol, fructose, maltose, and mannose), stabilizers (e.g., sodium sulfite and albumin), preservatives (e.g., benzyl alcohol, methyl p-oxybenzoate) can be incorporated as appropriate.

The dosage of a compound of formula (I) of the present invention or a pharmaceutically acceptable salt thereof can be varied according to the severity of the disease, age and weight of the patients, dosage form, or the like. However, it can be administrated normally in a range of 1 mg to 1,000 mg per day in adults by oral or parenteral route in a single dose or in two or three divided doses.

In addition, a compound of formula (I) of the present invention or a pharmaceutically acceptable salt thereof can be used as a STING inhibitor and as a reagent for experiments or research.

A compound in which a compound of formula (I) of the present invention is radiolabeled can also be used as a molecular probe for PET.

In some embodiments, the present invention provides method of inhibiting activation of a STING pathway (e.g., by inhibiting STING or cGAS) in a patient or biological sample comprising administering to said patient, or contacting said biological sample with a compound of formula (I), a pharmaceutically acceptable salt thereof, or a pharmaceutical composition thereof.

In some embodiments, the present invention provides a method of treating a disease associated with STING-mediated cellular responses (e.g., by inhibiting STING or cGAS) in a patient comprising administering to said patient a compound of formula (I), a pharmaceutically acceptable salt thereof, or a pharmaceutical composition thereof.

In some embodiments, the disease associated with STING-mediated cellular responses is selected from inflammatory disease, autoimmune disease, cardiovascular disease, pulmonary disease, metabolic disease, neurodegenerative disease, viral infection, ophthalmologic disease, and cancer.

In some embodiments, the present invention provides a method of treating inflammatory disease in a patient comprising administering to said patient a compound of formula (I), a pharmaceutically acceptable salt thereof, or a pharmaceutical composition thereof.

In some embodiments, the present invention provides a method of treating autoimmune disease in a patient comprising administering to said patient a compound of formula (I), a pharmaceutically acceptable salt thereof, or a pharmaceutical composition thereof.

In some embodiments, the present invention provides a method of treating cardiovascular disease in a patient comprising administering to said patient a compound of formula (I), a pharmaceutically acceptable salt thereof, or a pharmaceutical composition thereof.

In some embodiments, the present invention provides a method of treating pulmonary disease in a patient comprising administering to said patient a compound of formula (I), a pharmaceutically acceptable salt thereof, or a pharmaceutical composition thereof.

In some embodiments, the present invention provides a method of treating metabolic disease in a patient comprising administering to said patient a compound of formula (I), a pharmaceutically acceptable salt thereof, or a pharmaceutical composition thereof.

In some embodiments, the present invention provides a method of treating neurodegenerative disease in a patient comprising administering to said patient a compound of formula (I), a pharmaceutically acceptable salt thereof, or a pharmaceutical composition thereof.

In some embodiments, the present invention provides a method of treating viral infection in a patient comprising administering to said patient a compound of formula (I), a pharmaceutically acceptable salt thereof, or a pharmaceutical composition thereof.

In some embodiments, the present invention provides a method of treating ophthalmologic disease in a patient comprising administering to said patient a compound of formula (I), a pharmaceutically acceptable salt thereof, or a pharmaceutical composition thereof.

In some embodiments, the present invention provides a method of treating cancer in a patient comprising administering to said patient a compound of formula (I), or a pharmaceutically acceptable salt thereof, or a pharmaceutical composition thereof.

In some embodiments, the disease associated with STING-mediated cellular responses (e.g., STING or cGAS-associated disease) is STING-associated vasculopathy with onset in infancy (SAVI), familial lupus-like syndrome, Aicardi-Goutières syndrome (AGS), systemic lupus erythematosus (SLE) (e.g., lupus nephritis, familial chilblain lupus), sepsis, alcohol liver disease (ALD), non-alcoholic fatty liver disease (NAFLD), non-alcoholic steatohepatitis (NASH), pancreatitis (e.g., acute), dermatomyositis, macular degeneration (e.g., dry age-related macular degeneration), psoriasis, Sjogren's syndrome, Niemann-Pick disease (e.g., Type C), interferonopathies (e.g., rare Type 1 interferonopathy), infarction (e.g., myocardial infarction), heart failure, cardiomyopathy, intestinal inflammation (e.g., inflammatory bowel disease (IBD), ulcerative colitis (UC), Crohn's disease (CD), irritable bowel syndrome (IBS)), cellular senescence, ageing, COPA syndrome, acute kidney injury (AKI), fibrosis (e.g., kidney, lung, liver), acne, amyotrophic lateral sclerosis (ALS), Parkinson's disease (PD), Alzheimer's disease (AD), kidney disease (e.g., chronic kidney disease), obesity, arthritis (e.g., polyarthritis, rheumatoid arthritis), viral hepatitis, and COVID-19 (e.g., see Non Patent Literature 16).

In some embodiments, the present invention provides a method of treating STING-associated vasculopathy with onset in infancy (SAVI) in a patient comprising administering to said patient a compound of formula (I), a pharmaceutically acceptable salt thereof, or a pharmaceutical composition thereof.

In some embodiments, the present invention provides a method of treating familial lupus-like syndrome in a patient comprising administering to said patient a compound of formula (I), a pharmaceutically acceptable salt thereof, or a pharmaceutical composition thereof.

In some embodiments, the present invention provides a method of treating Aicardi-Goutières syndrome (AGS) in a patient comprising administering to said patient a compound of formula (I), a pharmaceutically acceptable salt thereof, or a pharmaceutical composition thereof.

In some embodiments, the present invention provides a method of treating systemic lupus erythematosus (SLE) (e.g., lupus nephritis, familial chilblain lupus) in a patient comprising administering to said patient a compound of formula (I), a pharmaceutically acceptable salt thereof, or a pharmaceutical composition thereof.

In some embodiments, the present invention provides a method of treating sepsis in a patient comprising administering to said patient a compound of formula (I), a pharmaceutically acceptable salt thereof, or a pharmaceutical composition thereof.

In some embodiments, the present invention provides a method of treating alcohol liver disease (ALD) in a patient comprising administering to said patient a compound of formula (I), a pharmaceutically acceptable salt thereof, or a pharmaceutical composition thereof.

In some embodiments, the present invention provides a method of treating nonalcoholic fatty liver disease (NAFLD) in a patient comprising administering to said patient a compound of formula (I), a pharmaceutically acceptable salt thereof, or a pharmaceutical composition thereof.

In some embodiments, the present invention provides a method of treating non-alcoholic steatohepatitis (NASH) in a patient comprising administering to said patient a compound of formula (I), a pharmaceutically acceptable salt thereof, or a pharmaceutical composition thereof.

In some embodiments, the present invention provides a method of treating pancreatitis (e.g., acute) in a patient comprising administering to said patient a compound of formula (I), a pharmaceutically acceptable salt thereof, or a pharmaceutical composition thereof.

In some embodiments, the present invention provides a method of treating dermatomyositis in a patient comprising administering to said patient a compound of formula (I), a pharmaceutically acceptable salt thereof, or a pharmaceutical composition thereof.

In some embodiments, the present invention provides a method of treating macular degeneration (e.g., dry age-related macular degeneration) in a patient comprising administering to said patient a compound of formula (I), a pharmaceutically acceptable salt thereof, or a pharmaceutical composition thereof.

In some embodiments, the present invention provides a method of treating psoriasis in a patient comprising administering to said patient a compound of formula (I), a pharmaceutically acceptable salt thereof, or a pharmaceutical composition thereof.

In some embodiments, the present invention provides a method of treating Sjogren's syndrome in a patient comprising administering to said patient a compound of formula (I), a pharmaceutically acceptable salt thereof, or a pharmaceutical composition thereof.

In some embodiments, the present invention provides a method of treating Niemann-Pick disease (e.g., Type C) in a patient comprising administering to said patient a compound of formula (I), a pharmaceutically acceptable salt thereof, or a pharmaceutical composition thereof.

In some embodiments, the present invention provides a method of treating interferonopathies (e.g., rare Type 1 interferonopathy) in a patient comprising administering to said patient a compound of formula (I), a pharmaceutically acceptable salt thereof, or a pharmaceutical composition thereof.

In some embodiments, the present invention provides a method of treating infarction (e.g., myocardial infarction) in a patient comprising administering to said patient a compound of formula (I), a pharmaceutically acceptable salt thereof, or a pharmaceutical composition thereof.

In some embodiments, the present invention provides a method of treating heart failure in a patient comprising administering to said patient a compound of formula (I), a pharmaceutically acceptable salt thereof, or a pharmaceutical composition thereof.

In some embodiments, the present invention provides a method of treating cardiomyopathy in a patient comprising administering to said patient a compound of formula (I), a pharmaceutically acceptable salt thereof, or a pharmaceutical composition thereof.

In some embodiments, the present invention provides a method of treating intestinal inflammation (e.g., inflammatory bowel disease (IBD), ulcerative colitis (UC), Crohn's disease (CD), irritable bowel syndrome (IBS)) in a patient comprising administering to said patient a compound of formula (I), a pharmaceutically acceptable salt thereof, or a pharmaceutical composition thereof.

In some embodiments, the present invention provides a method of treating cellular senescence in a patient comprising administering to said patient a compound of formula (I), a pharmaceutically acceptable salt thereof, or a pharmaceutical composition thereof.

In some embodiments, the present invention provides a method of treating ageing in a patient comprising administering to said patient a compound of formula (I), a pharmaceutically acceptable salt thereof, or a pharmaceutical composition thereof.

In some embodiments, the present invention provides a method of treating COPA syndrome in a patient comprising administering to said patient a compound of formula (I), a pharmaceutically acceptable salt thereof, or a pharmaceutical composition thereof.

In some embodiments, the present invention provides a method of treating acute kidney injury (AKI) in a patient comprising administering to said patient a compound of formula (I), a pharmaceutically acceptable salt thereof, or a pharmaceutical composition thereof.

In some embodiments, the present invention provides a method of treating fibrosis (e.g., kidney, lung, liver) in a patient comprising administering to said patient a compound of formula (I), a pharmaceutically acceptable salt thereof, or a pharmaceutical composition thereof.

In some embodiments, the present invention provides a method of treating acne in a patient comprising administering to said patient a compound of formula (I), a pharmaceutically acceptable salt thereof, or a pharmaceutical composition thereof.

In some embodiments, the present invention provides a method of treating amyotrophic lateral sclerosis (ALS) in a patient comprising administering to said patient a compound of formula (I), a pharmaceutically acceptable salt thereof, or a pharmaceutical composition thereof.

In some embodiments, the present invention provides a method of treating Parkinson's disease (PD) in a patient comprising administering to said patient a compound of formula (I), a pharmaceutically acceptable salt thereof, or a pharmaceutical composition thereof.

In some embodiments, the present invention provides a method of treating Alzheimer's disease (AD) in a patient comprising administering to said patient a compound of formula (I), a pharmaceutically acceptable salt thereof, or a pharmaceutical composition thereof.

In some embodiments, the present invention provides a method of treating kidney disease (e.g., chronic kidney disease) in a patient comprising administering to said patient a compound of formula (I), a pharmaceutically acceptable salt thereof, or a pharmaceutical composition thereof.

In some embodiments, the present invention provides a method of treating obesity in a patient comprising administering to said patient a compound of formula (I), a pharmaceutically acceptable salt thereof, or a pharmaceutical composition thereof.

In some embodiments, the present invention provides a method of treating arthritis (e.g., polyarthritis, rheumatoid arthritis) in a patient comprising administering to said patient a compound of formula (I), a pharmaceutically acceptable salt thereof, or a pharmaceutical composition thereof.

In some embodiments, the present invention provides a method of treating viral hepatitis in a patient comprising administering to said patient a compound of formula (I), a pharmaceutically acceptable salt thereof, or a pharmaceutical composition thereof.

In some embodiments, the present invention provides a method of treating COVID-19 in a patient comprising administering to said patient a compound of formula (I), a pharmaceutically acceptable salt thereof, or a pharmaceutical composition thereof.

In some embodiments, the present invention provides a method of suppressing STING-promoted cytokine production in a patient comprising administering to said patient a compound of formula (I), a pharmaceutically acceptable salt thereof, or a pharmaceutical composition thereof. In some embodiments a compound of formula (I) or a pharmaceutically acceptable salt thereof of the present invention suppresses the production of IFN-β and IL-6 in a patient.

In some embodiments, the present invention provides a method of suppressing wild type STING activation in a patient comprising administering to said patient a compound of formula (I), a pharmaceutically acceptable salt thereof, or a pharmaceutical composition thereof.

In some embodiments, the present invention provides a method of suppressing mutant STING activation in a patient comprising administering to said patient a compound of formula (I), a pharmaceutically acceptable salt thereof, or a pharmaceutical composition thereof.

In some embodiments, the present invention provides a method of suppressing elevated cGAS levels in a patient comprising administering to said patient a compound of formula (I), a pharmaceutically acceptable salt thereof, or a pharmaceutical composition thereof.

In some embodiments, the method of suppressing wild type or mutant STING activation, or elevated cGAS levels in a patient, may be determined by measuring clinical biomarkers in the patient.

Combination Therapies

In some embodiments, a compound of formula (I) or a pharmaceutically acceptable salt thereof can be administered in combination with one or more additional therapeutic agents and/or regimens. For example, the methods of treating a disease associated with STING-mediated cellular responses (e.g., STING or cGAS-associated disease) provided herein can further include administering one or more (e.g., two, three, four, five, six, or more) additional therapeutic agents.

Additional therapeutic agents of the invention may include, but are not limited to, small molecules or recombinant biologic agents, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Araya®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret R) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and/or dexamethasone (Decadron®) in combination with lenalidomide (Revlimid®), or any combination(s) thereof.

In some embodiments, the present invention provides a method of treating inflammatory or autoimmune disease comprising administering to a patient in need thereof a compound of formula (I) or a pharmaceutically acceptable salt thereof and one or more additional therapeutic agents selected from, but not limited to gamma globulin, immunomodulatory and immunosuppressive compounds (for example, cyclosporine, Methotrexate®), TNF antagonists (for example, Humira®, etanercept, infliximab), IL-1 inhibitors (for example, anakinra, canakinumab, rilonacept), phosphodiesterase inhibitors (for example, apremilast), JAK/STAT inhibitors (for example, tofacitinib, baricitinib, GLPG0634), IRAK4 inhibitors, leflunomide, cyclophosphamide, rituximab, belimumab, tacrolimus, rapamycin, mycophenolate mofetil, interferon, corticosteroids (for example, prednisone, prednisolone, methylprednisolone, hydrocortisone, betamethasone), cyclophosphamide, azathioprine, sulfasalazine, paracetamol, and/or a non-steroidal anti-inflammatory agent (NSAID) (for example, aspirin, ibuprofen, naproxen, etodolac, celecoxib, colchicine).

In some embodiments, the present invention provides a method of treating STING-associated vasculopathy with onset in infancy (SAVI) comprising administering to a patient in need thereof a compound of formula (I) or a pharmaceutically acceptable salt thereof and one or more additional therapeutic agents selected from JAK inhibitors (e.g., tofacitinib, ruxolitinib, filgotinib, and baricitinib).

In some embodiments, the present invention provides a method of treating Aicardi-Goutières syndrome (AGS) comprising administering to a patient in need thereof a compound of formula (I) or a pharmaceutically acceptable salt thereof and one or more additional therapeutic agents and/or regimens selected from physiotherapy, treatment for respiratory complications, anticonvulsant therapies for seizures, tube-feeding, nucleoside reverse transcriptase inhibitors (e.g., emtricitabine (e.g., Emtriva®), tenofovir (e.g., Viread®), emtricitabine/tenofovir (e.g., Truvada®), zidovudine, lamivudine, and abacavir), and JAK inhibitors (e.g., tofacitinib, ruxolitinib, filgotinib, and baricitinib).

In some embodiments, the present invention provides a method of treating familial lupus-like syndrome or systemic lupus erythematosus (SLE) (e.g., lupus nephritis, familial chilblain lupus) comprising administering to a patient in need thereof a compound of formula (I) or a pharmaceutically acceptable salt thereof and one or more additional therapeutic agents selected from steroids, topical immunomodulators (e.g., tacrolimus ointment (Protopic®) and pimecrolimus cream (Elidel®)), thalidomide (Thalomid®), non-steroidal anti inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., evobrutinib, iberdomide, voclosporin, cenerimod, azathioprine (Imuran®), cyclophosphamide (Cytoxan®, Neosar®, Endoxan®), and cyclosporine (Neoral, Sandimmune®, Gengraf®), and mycophenolate mofetil) baricitinb, iguratimod, filogotinib, GS-9876, rapamycin, and PF-06650833), and biologies (e.g., belimumab (Benlysta®), anifrolumab, prezalumab, MEDI0700, obinutuzumab, vobarilizumab, lulizumab, atacicept, PF-06823859, and lupizor, rituximab, BT063, BI655064, BIIB059, aldesleukin (Proleukin®), dapirolizumab, edratide, IFN-a-kinoid, OMS721, RC18, RSLY-132, theralizumab, XmAb5871, and ustekinumab (Stelara®)). For example, non-limiting treatments for systemic lupus erythematosus include non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., iberdomide, voclosporin, azathioprine (Imuran®), cyclophosphamide (Cytoxan®, Neosar®, Endoxan®), and cyclosporine (Neoral, Sandimmune®, Gengraf®), and mycophenolate mofetil, baricitinb, filogotinib, and PF-06650833), and biologies (e.g., belimumab (Benlysta®), anifrolumab, prezalumab, MEDI0700, vobarilizumab, lulizumab, atacicept, PF-06823859, lupizor, rituximab, BT063, BI655064, BIIB059, aldesleukin (Proleukin®), dapirolizumab, edratide, IFN-a-kinoid, RC18, RSLV-132, theralizumab, XmAb5871, and ustekinumab (Stelara®)).

In some embodiments, the present invention provides a method of treating arthritis (e.g., rheumatoid arthritis) comprising administering to a patient in need thereof a compound of formula (I) and one or more additional therapeutic agents selected from, but not limited to non-steroidal anti-inflammatory drugs (NSAIDS) such as but not limited to aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Araya®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and/or "anti-IL-6" agents such as tocilizumab (Actemra®).

In some embodiments, the present invention provides a method of treating inflammatory bowel disease (IBD) comprising administering to a patient in need thereof a compound of formula (I) and one or more additional therapeutic agents selected from, but not limited to 6-mercaptopurine, AbGn-168H, ABX464, ABT-494, adalimumab, AJM300, alicaforsen, AMG139, anrukinzumab, apremilast, ATR-107 (PF0530900), autologous CD34-selected peripheral blood stem cells transplant, azathioprine, bertilimumab, BI 655066, BMS-936557, certolizumab pegol (Cimzia®), cobitolimod, corticosteroids (e.g., prednisone, Methylprednisolone, prednisone), CP-690,550, CT-P13, cyclosporine, DIMS0150, E6007, E6011, etrasimod, etrolizumab, fecal microbial transplantation, figlotinib, fmgolimod, firategrast (SB-683699) (formerly T-0047), GED0301, GLPG0634, GLPG0974, guselkumab, golimumab, GSK 1399686, HMPL-004 (*Andrographis paniculata* extract), I1V1U-838, infliximab, Interleukin 2 (IL-2), Janus kinase (JAK) inhibitors, laquinimod, masitinib (AB1010), matrix metalloproteinase 9 (MMP 9) inhibitors (e.g., GS-5745), MEDI2070, mesalamine, methotrexate, mirikizumab (LY3074828), natalizumab, NNC 0142-0000-0002, NNC0114-0006, ozanimod, peficitinib (JNJ-54781532), PF-00547659, PF-04236921, PF-06687234, QAX576, RHB-104, rifaximin, risankizumab, RPC1063, SB012, SHP647, sulfasalazine, TD-1473, thalidomide, tildrakizumab (MK 3222), TJ301, TNF-Kinoid®, tofacitinib, tralokinumab, TRK-170, upadacitinib, ustekinumab, UTTR1147A, V565, vatelizumab, VB-201, vedolizumab, and vidofludimus.

In some embodiments, the present invention provides a method of treating Crohn's disease (CD) comprising administering to a patient in need thereof a compound of formula (I) and one or more additional therapeutic agents selected from, but not limited to adalimumab, autologous CD34-selected peripheral blood stem cells transplant, 6-mercaptopurine, azathioprine, certolizumab pegol (Cimzia®), corticosteroids (e.g., prednisone), etrolizumab, E6011, fecal microbial transplantation, figlotinib, guselkumab, infliximab, IL-2, JAK inhibitors, matrix metalloproteinase 9 (MMP 9) inhibitors (e.g., GS-5745), MEDI2070, mesalamine, methotrexate, natalizumab, ozanimod, RHB-104, rifaximin, risankizumab, SHP647, sulfasalazine, thalidomide, upadacitinib, V565, and vedolizumab.

In some embodiments, the present invention provides a method of treating ulcerative colitis (UC) comprising administering to a patient in need thereof a compound of formula (I) and one or more additional therapeutic agents selected from, but not limited to AbGn-168H, ABT-494, ABX464, apremilast, PF-00547659, PF-06687234, 6-mercaptopurine, adalimumab, azathioprine, bertilimumab, brazikumab (MEDI2070), cobitolimod, certolizumab pegol (Cimzia®), CP-690,550, corticosteroids (e.g., multimax budesonide, Methylprednisolone), cyclosporine, E6007, etrasimod, etrolizumab, fecal microbial transplantation, figlotinib, guselkumab, golimumab, IL-2, IMU-838, infliximab, matrix metalloproteinase 9 (MMP9) inhibitors (e.g., GS-5745), mesalamine, mesalamine, mirikizumab (LY3074828), RPC1063, risankizumab (BI 6555066), SHP647, sulfasalazine, TD-1473, TJ301, tildrakizumab (MK 3222), tofacitinib, tofacitinib, ustekinumab, UTTR1147A, and vedolizumab.

In some embodiments, the present invention provides a method of treating irritable bowel syndrome (IBS) comprising administering to a patient in need thereof a compound of formula (I) and one or more additional therapeutic agents selected from, but not limited to alosetron, bile acid sequestrants (e.g., cholestyramine, colestipol, colesevelam), chloride channel activators (e.g., lubiprostone), coated peppermint oil capsules, desipramine, dicyclomine, ebastine, eluxadoline, farnesoid X receptor agonist (e.g., obeticholic acid), fecal microbiota transplantation, fluoxetine, gabapentin, guanylate cyclase-C agonists (e.g., linaclotide, plecanatide), ibodutant, imipramine, JCM-16021, loperamide, lubiprostone, nortriptyline, ondansetron, opioids, paroxetine, pinaverium, polyethylene glycol, pregabalin, probiotics, ramosetron, rifaximin, and tanpanor.

In some embodiments, the present invention provides a method of treating psoriasis comprising administering to a patient in need thereof a compound of formula (I) and one or more additional therapeutic agents selected from, but not limited to topical corticosteroids, topical crisaborole/AN2728, topical SNA-120, topical SAN021, topical tapinarof, topical tocafmib, topical IDP-118, topical M518101, topical calcipotriene and betamethasone dipropionate (e.g., MC2-01 cream and Taclonex®), topical P-3073, topical LEO 90100 (Enstilar®), topical betamethasone dipropriate (Semivo®), halobetasol propionate (Ultravate®), vitamin D analogues (e.g., calcipotriene (Dovonex®) and calcitriol (Vectical®)), anthralin (e.g., Dritho-scalp® and Dritho-creme®), topical retinoids (e.g., tazarotene (e.g., Tazorac® and Avage®)), calcineurin inhibitors (e.g., tacrolimus (Prograf®) and pimecrolimus (Elidel®)), salicylic acid, coal tar, moisturizers, phototherapy (e.g., exposure to sunlight, UVB phototherapy, narrow band UVB phototherapy, Goeckerman therapy, psoralen plus ultraviolet A (PUVA) therapy, and excimer laser), retinoids (e.g., acitretin (Soriatane®)), methotrexate (Trexall®, Otrexup®, Rasuvo®, Rheumatrex®), Apo805K1, baricitinib, FP187, KD025, prurisol, VTP-43742, XP23829, ZPL-389, CF101 (piclidenoson), LAS41008, VPD-737 (serlopitant), upadacitinib (ABT-494), aprmilast, tofacitibin, cyclosporine (Neoral®, Sandimmune®, Gengraf®), biologies (e.g., etanercept (Enbrel®), entanercept-szzs (Elrezi®), infliximab (Remicade®), adalimumab (Humira®), adalimumab-adbm (Cyltezo®), ustekinumab (Stelara®), golimumab (Simponi®), apremilast (Otezla®), secukinumab (Cosentyx®), certolizumab pegol, secukinumab, tildrakizumab-asmn, infliximab-dyyb, abatacept, ixekizumab (Taltz®), ABP 710, BCD-057, BI695501, bimekizumab (UCB4940), CHS-1420, GP2017, guselkumab (CNTO 1959), HD203, M923, MSB 11022, Mirikizumab (LY3074828), PF-06410293, PF-06438179, risankizumab (BI655066), SB2, SB4, SB5, siliq (brodalumab), namilumab (MT203, tildrakizumab (MK-3222), and ixekizumab (Taltz®)), thioguanine, and hydroxyurea (e.g., Droxia® and Hydrea®).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a disease associated with STING-mediated cellular responses (e.g., STING or cGAS-associated disease).

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including emactuzumab (RG7155).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is atezolizumab (RG7446), durvalumab (MEDI4736), BMS-936559 (WO2007/005874), and avelumab (MSB0010718C).

In some embodiments, an immuno-oncology agent is a LAG-3 antagonist. In some embodiments, a LAG-3 antagonist is an antagonistic LAG-3 antibody. In some embodiments, a LAG3 antibody is relatlimab (BMS-986016), or IMP-731 or eftilagimod alpha (IMP-321).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or utomilumab (PF-05082566).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO2006/105021, WO2009/009116), or MK-4166 (WO2011/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO2009/073620, WO2009/115665, WO2011/056652, WO2012/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is vonlerolizumab (RG-7888).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is enoblituzumab (MGA271) (to B7H3).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Hundreds of clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the contents of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

5. Further Embodiments

Further embodiments of the present invention are described below. These embodiments are illustrative and should not be construed as limiting the scope of the claimed invention.

Embodiment 1. A 1,2-diaminobenzimidazole derivative represented by the following formula (I):

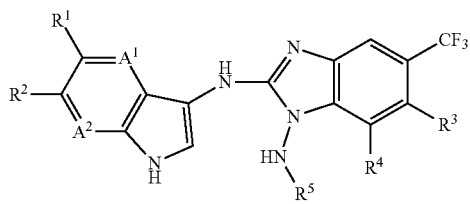

(I)

or a pharmaceutically acceptable salt thereof, wherein:
$A^1$ represents a nitrogen atom or C—$R^6$;
$A^2$ represents a nitrogen atom or C—$R^7$;
$R^1$ represents a halogen atom or an alkyl group;
each of $R^2$, $R^3$, $R^4$, $R^6$, and $R^7$ independently represents a hydrogen atom or a fluorine atom, and
$R^5$ represents a hydrogen atom or an optionally substituted alkyl group.

Embodiment 2. A compound described in any of Examples 1 to 29 or a pharmaceutically acceptable salt thereof.

EXEMPLIFICATION

The present invention is described in more detail below including Examples and Test Examples, but the present invention is not limited by these Examples.

The compounds were identified by hydrogen-nuclear magnetic resonance spectroscopy (1H-NMR) and mass spectroscopy (MS). $^1$H-NMR is measured at 400 MHz unless otherwise indicated, and exchangeable hydrogen may not be clearly observed depending on the compound and measurement conditions. Note that brs means a wide range of signals (broad). HPLC preparative chromatography was performed using a commercially available ODS column in gradient mode with water/acetonitrile (containing formic acid) or water/methanol (containing formic acid) as eluates.

Reference Example 1. Production of 5-chloro-3-isothiocyanato-1H-indole

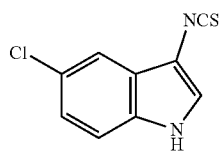

Chemical Formula 10

(Step 1) Production of N-(5-chloro-1H-indol-3-yl)-2,2,2-trifluoroacetamide

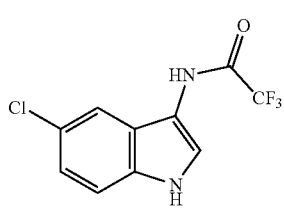

Chemical Formula 11

Trifluoroacetic anhydride (51.87 g, 247 mmol) was added dropwise to a THF solution (210 mL) of 2,2-diethoxyethane-1-amine (30 g, 225 mmol) and DIPEA (34.92 g, 270 mmol), and a residual reagent was added dropwise to a dropping funnel by adding THF (30 mL). After stirred at room temperature for 1 hour, the reaction mixture was washed twice with a mixture of water (88 mL), concentrated hydrochloric acid (8 mL), and sodium chloride (4.8 g), and the organic layer was distilled off under reduced pressure. The resulting residue (34.9 g) was dissolved in a mixed solvent of 1,2-dichloroethane/toluene (1:1, 240 mL), and 4-chlorophenylhydrazine hydrochloride (36.41 g, 203 mmol) was added to this solution and stirred at 50° C. for 1 hour. After cooling the reaction mixture to room temperature, water (60 mL) was added. After cooling to 0° C., a precipitated solid was filtered off. The solid was washed with water and then with a mixed solvent of 1,2-dichloroethane/toluene (1:1, 30 mL). To the resulting solid, a 2-propanol aqueous solution (20%, 250 mL) was added and cooled to 0° C., and then the solid was filtered off and dried to obtain the title compound (28.07 g). $^1$H NMR (DMSO-$d_6$) δ 11.39 (s, 1H), 11.28 (s, 1H), 7.93-7.87 (m, 1H), 7.82 (d, J=2.6 Hz, 1H), 7.42 (d, J=8.7 Hz, 1H), 7.14 (dd, J=8.7, 2.1 Hz, 1H); LCMS (m/z) 261.0 [M−H]−

(Step 2) Production of 5-chloro-1H-indol-3-amine Hydrochloride

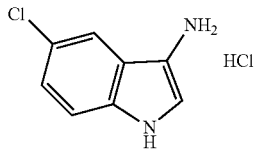

Chemical Formula 12

A mixture of N-(5-chloro-1H-indol-3-yl)-2,2,2-trifluoroacetamide (7.1 g, 27 mmol) and 2N hydrochloric acid/ethanol solution (70 mL) was stirred at 80° C. overnight. The solvent was distilled off under reduced pressure, ethyl acetate was added to the resulting residue, and the solid was filtered off and dried to obtain the title compound (4.96 g). $^1$H NMR (DMSO-$d_6$) δ 11.63 (s, 1H), 10.35 (brs, 3H), 7.72 (d, J=2.0 Hz, 1H), 7.58 (d, J=2.8 Hz, 1H), 7.47 (d, J=8.7 Hz, 1H), 7.19 (dd, J=8.7, 2.1 Hz, 1H); LCMS (m/z) 167.0 [M+H]+.

(Step 3) Production of 5-chloro-3-isothiocyanato-1H-indole. To a THF solution (100 mL) of 5-chloro-1H-indol-3-amine hydrochloride (4.96 g, 24.43 mmol), thiophosgene (3.09 g, 26.9 mmol) and DIPEA (6.31 g, 48.9 mmol) were added, and the mixture was stirred at room temperature for 50 minutes. Ethyl acetate was added to the reaction mixture and washed with dilute hydrochloric acid and saturated saline in order, and then the organic layer was dried over anhydrous sodium sulfate. The solvent was distilled off under reduced pressure to obtain the title compound (5.04 g). $^1$H NMR (DMSO-$d_6$) δ 11.76 (s, 1H), 7.84 (d, J=2.9 Hz, 1H), 7.63-7.55 (m, 1H), 7.48 (dd, J=8.7 Hz, 0.7 Hz, 1H), 7.24 (dd, J=8.7, 2.0 Hz, 1H); LCMS (m/z) 207.1 [M−H]−

Reference Example 2. Production of tert-butyl 2-[2-amino-4-(trifluoromethyl)phenyl]hydrazine-1-carboxylate Chemical Formula 13

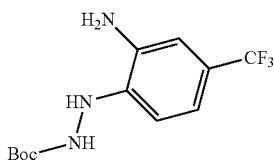

(Step 1) Production of tert-butyl 2-[2-nitro-4-(trifluoromethyl)phenyl]hydrazine-1-carboxylate Chemical Formula 14

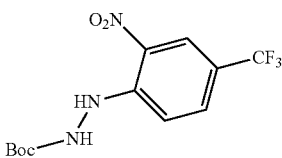

To a NMP solution (50 mL) of 1-fluoro-2-nitro-4-(trifluoromethyl)benzene (10 g, 47.8 mmol), tert-butylhydrazinecarboxylate (9.48 g, 71.7 mmol) was added and stirred at 80° C. overnight. The reaction mixture was diluted with water and then extracted with ethyl acetate. The resulting organic layer was washed with saturated saline and dried over anhydrous sodium sulfate, and then the solvent was distilled off under reduced pressure to obtain the title compound (15.36 g). 1H NMR (Chloroform-d) δ 9.15 (s, 1H), 8.50-8.45 (m, 1H), 7.72 (dd, J=9.0, 2.1 Hz, 1H), 7.34 (d, J=9.0 Hz, 1H), 6.44 (s, 1H), 1.49 (s, 9H).

(Step 2) Production of tert-butyl 2-[2-amino-4-(trifluoromethyl)phenyl]hydrazine-1-carboxylate. Tert-butyl 2-[2-nitro-4-(trifluoromethyl)phenyl]hydrazine-1-carboxylate (15.36 g, 47.8 mmol) was dissolved in a mixed solvent of methanol/THF/saturated aqueous ammonium chloride solution (1:1:1, 300 mL), and zinc powder (15.63 g, 239 mmol) was added thereto at 0° C. and stirred at 0° C. for 20 minutes. The reaction mixture was filtered through Celite to remove insoluble materials. The organic layer was concentrated under reduced pressure, and the remaining aqueous layer was extracted with ethyl acetate. Subsequently, it was washed with saturated saline and dried over anhydrous sodium sulfate, and then the solvent was distilled off under reduced pressure to obtain the title compound (12.49 g). $^1$H NMR (DMSO-d$_6$) δ 8.89 (s, 1H), 7.15 (d, J=2.1 Hz, 1H), 6.85-6.77 (m, 2H), 6.59 (d, J=8.2 Hz, 1H), 5.02 (s, 2H), 1.42 (s, 9H).

Reference Example 3. Production of 5,6-difluoro-3-isothiocyanato-1H-indole

Chemical Formula 15

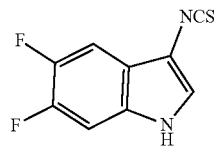

(Step 1) Production of 5,6-difluoro-3-nitro-1H-indole

Chemical Formula 16

An acetic acid solution (9 mL) of fuming nitric acid (1.296 g, 20.57 mmol) was added dropwise to an acetic acid solution (15 mL) of 5,6-difluoro-1H-indole (3 g, 19.59 mmol) and acetic anhydride (4.32 g, 42.3 mmol) at 0° C. and stirred at room temperature for 4 hours. Water (30 mL) was added to the reaction mixture to stop the reaction, and acetic acid (4 mL) was added thereto. After cooling to 0° C., a precipitated solid was filtered off. The solid was purified by amine-modified silica gel chromatography (hexane:ethyl acetate=1:0 to 0:1) to obtain the title compound (1.94 g). $^1$H NMR (DMSO-d$_6$) δ 12.81 (s, 1H), 8.71 (s, 1H), 7.97 (dd, J=10.8 Hz, 7.9 Hz, 1H), 7.66 (dd, J=10.4, 6.8 Hz, 1H); LCMS (m/z) 197.1 [M−H]−

(Step 2) Production of tert-butyl (5,6-difluoro-1H-indol-3-yl)carbamate

Chemical Formula 17

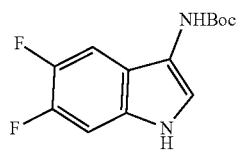

To a mixed solvent of methanol/THF/saturated aqueous ammonium chloride solution (1:1:1, 60 mL), 5,6-difluoro-3-nitro-1H-indole (1.9 g, 9.59 mmol) was added. After zinc powder (6.27 g, 96 mmol) was added to this suspension at 0° C. and stirred at 0° C. for 5 minutes, Boc2O (2.512 g, 11.51 mmol) was added thereto and stirred at 0° C. for 30 minutes, and then stirred at room temperature for 1 hour. In order to complete the reaction, zinc powder (2.7 g, 41.3 mmol) was put therein and further stirred at room temperature for 3 hours. The reaction mixture was filtered through Celite to remove insoluble materials. The filtrate was concentrated under reduced pressure, and the residue was purified by silica gel chromatography (hexane:ethyl acetate=1:0 to 7:3) to obtain the title compound (1.16 g). $^1$H NMR (DMSO-d6) δ 10.87 (s, 1H), 9.18 (s, 1H), 7.73 (dd, J=11.6, 8.2 Hz, 1H), 7.47 (s, 1H), 7.29 (dd, J=11.3, 7.0 Hz, 1H), 1.49 (s, 9H); LCMS (m/z) 267.1 [M−H]−.

(Step 3) Production of
5,6-difluoro-1H-indol-3-amine Hydrochloride

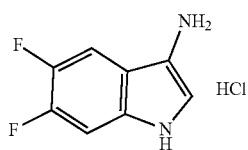

Chemical Formula 18

A mixture of tert-butyl (5,6-difluoro-1H-indol-3-yl)carbamate (1.16 g, 4.32 mmol) and 4N hydrochloric acid/ethyl acetate solution (10 mL) was stirred at room temperature for 1 hour. A precipitated solid was filtered off and dried to obtain the title compound (650 mg). $^1$H NMR (DMSO-d$_6$) δ 11.59-11.54 (m, 1H), 10.14 (brs, 3H), 7.61 (dd, J=11.1, 7.9 Hz, 1H), 7.57 (d, J=2.8 Hz, 1H), 7.49 (dd, J=11.1, 7.0 Hz, 1H); LCMS (m/z) 169.1 [M+H]+.

(Step 4) Production of 5,6-difluoro-3-isothiocyanato-1H-indole. To a THF solution (15 mL) of 5,6-difluoro-1H-indol-3-amine hydrochloride (650 mg, 3.18 mmol), thiophosgene (402 mg, 3.49 mmol) and DIPEA (821 mg, 6.35 mmol) were added and stirred at room temperature for 2 hours. In order to complete the reaction, thiophosgene (402 mg, 3.49 mmol) and DIPEA (821 mg, 6.35 mmol) were put therein and further stirred at room temperature for 1.5 hours. Ethyl acetate and saturated saline were added to the reaction mixture and filtered through Celite to remove insoluble materials. The filtrate was washed with water and saturated saline in order. The resulting organic layer was dried over anhydrous sodium sulfate, and then the solvent was distilled off under reduced pressure to obtain the title compound (668 mg). $^1$H NMR (DMSO-d$_6$) δ 11.72 (s, 1H), 7.85 (d, J=2.9 Hz, 1H), 7.63-7.56 (m, 1H), 7.51 (dd, J=10.9, 6.8 Hz, 1H); LCMS (m/z) 209.1 [M−H]−.

Reference Example 4. Production of
4,5-difluoro-3-isothiocyanato-1H-indole

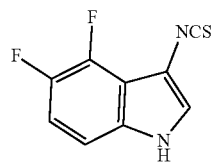

Chemical Formula 19

(Step 1) Production of
4,5-difluoro-3-nitro-1H-indole

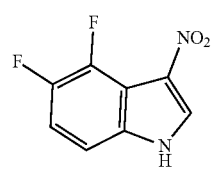

Chemical Formula 20

An acetic acid solution (9 mL) of fuming nitric acid (1.059 g, 16.8 mmol) was added dropwise to an acetic acid solution (15 mL) of 4,5-difluoro-1H-indole (2.45 g, 16 mmol) and acetic anhydride (3.528 g, 34.6 mmol) at 0° C. and stirred at room temperature for 1.5 hours. Water (30 mL) was added to the reaction mixture and cooled to 0° C., and then a precipitated solid was filtered off. The solid was purified by amine modified silica gel chromatography (hexane:ethyl acetate=1:0 to 0:1, subsequently ethyl acetate:methanol=9:1) to obtain the title compound (2.04 g). NMR (DMSO-d$_6$) δ 12.94 (s, 1H), 8.73 (s, 1H), 7.44-7.35 (m, 2H); LCMS (m/z) 197.1 [M−H]−.

(Step 2) Production of tert-butyl
(4,5-difluoro-1H-indol-3-yl)carbamate

Chemical Formula 21

To a mixed solvent of methanol/THF/saturated aqueous ammonium chloride solution (1:1:1, 75 mL), 4,5-difluoro-3-nitro-1H-indole (2.04 g, 10.3 mmol) was added. After zinc powder (3.366 g, 51.5 mmol) was added to this suspension at 0° C. and stirred for 5 minutes, Boc$_2$O (2.472 g, 11.33 mmol) was added thereto and stirred at room temperature for 45 minutes. The reaction mixture was filtered through Celite to remove insoluble materials. The filtrate was concentrated under reduced pressure, and the residue was purified by amine-modified silica gel chromatography (hexane:ethyl acetate=1:0 to 1:1) to obtain the title compound (2.22 g). $^1$H NMR (DMSO-d$_6$) δ 11.20 (s, 1H), 8.40 (s, 1H), 7.30 (s, 1H), 7.16-7.01 (m, 2H), 1.45 (s, 9H); LCMS (m/z) 267.1 [M−H]−.

(Step 3) Production of
4,5-difluoro-1H-indol-3-amine Hydrochloride

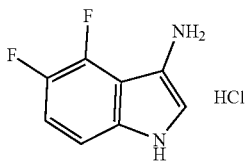

Chemical Formula 22

A mixture of tert-butyl (4,5-difluoro-1H-indol-3-yl)carbamate (2.22 g, 8.28 mmol) and 4N hydrochloric acid/ethyl acetate solution (10 mL) was stirred at room temperature for 30 minutes. A precipitated solid was filtered off and dried to obtain the title compound (1.35 g). $^1$H NMR (DMSO-d$_6$) δ 11.73 (s, 1H), 10.20 (brs, 3H), 7.59 (d, J=2.7 Hz, 1H), 7.35-7.20 (m, 2H); LCMS (m/z) 169.1 [M+H]+.

(Step 4) Production of 4,5-difluoro-3-isothiocyanato-1H-indole. To a THF solution (30 mL) of 4,5-difluoro-1H-indol-3-amine hydrochloride (1,348 mg, 6.59 mmol), thiophosgene (833 mg, 7.25 mmol) and DIPEA (1,703 mg, 13.18 mmol) were added and stirred at room temperature for 30 minutes. Ethyl acetate was added to the reaction mixture and washed with water and saturated saline in order. The resulting organic layer was dried over anhydrous sodium sulfate, and then the solvent was distilled off under reduced pressure to obtain the title compound (1,352 mg). $^1$H NMR (Chloroform-d) δ 8.08 (brs, 1H), 7.22 (d, J=2.8 Hz, 1H), 7.15-7.01 (m, 2H); LCMS (m/z) 209.1 [M−H]−.

Reference Example 5. Production of tert-butyl 2-[2-amino-4-(trifluoromethyl)phenyl]-1-methylhydrazine-1-carboxylate Chemical Formula 23

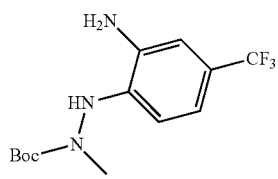

Production of tert-butyl 1-methyl-2-[2-nitro-4-(trifluoromethyl)phenyl]hydrazine-1-carboxylate Chemical Formula 24

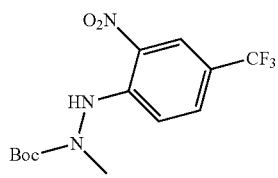

To a DMF solution (100 mL) of 1-fluoro-2-nitro-4-(trifluoromethyl)benzene (10 g, 47.8 mmol), tert-butyl 1-methylhydrazine-1-carboxylate (7.69 g, 52.6 mmol) and triethylamine (7.26 g, 71.7 mmol) were added and stirred at 100° C. for 2 hours. The reaction mixture was diluted with water and extracted twice with ethyl acetate. The resulting organic layer was washed with water and saturated saline in order and dried over anhydrous sodium sulfate. The solvent was distilled off under reduced pressure to obtain the title compound (16.3 g). $^1$H NMR (Chloroform-d) δ 9.31 (s, 1H), 8.49 (d, J=1.1 Hz, 1H), 7.71 (ddd, J=8.9, 1.5, 0.6 Hz, 1H), 7.08 (dd, J=9.1, 0.9 Hz, 1H), 3.26 (s, 3H), 1.42 (s, 9H); LCMS (m/z) 334.2 [M−H]−.

(Step 2) Production of tert-butyl 2-[2-amino-4-(trifluoromethyl)phenyl]-1-methylhydrazine-1-carboxylate. Tert-butyl 1-methyl-2-[2-nitro-4-(trifluoromethyl)phenyl]hydrazine-1-carboxylate (13.1 g, 38.3 mmol) was dissolved in a mixed solvent of methanol/THF/saturated aqueous ammonium chloride solution (5:5:4, 280 mL), and zinc powder (12.52 g, 191 mmol) was added thereto at 0° C. and stirred at 0° C. for 30 minutes. The reaction mixture was filtered through Celite to remove insoluble materials. The organic layer was concentrated under reduced pressure, and the remaining aqueous layer was extracted with ethyl acetate, subsequently washed with saturated saline, and dried over anhydrous sodium sulfate. The solvent was distilled off under reduced pressure to obtain the title compound (10.57 g). $^1$H NMR (Chloroform-d) δ 7.06 (d, J=8.4 Hz, 1H), 6.95 (d, J=1.9 Hz, 1H), 6.73 (d, J=8.2 Hz, 1H), 6.04 (s, 1H), 3.53 (brs, 2H), 3.19 (brs, 3H), 1.42 (brs, 9H).

Reference Example 6. Production of 5,7-difluoro-3-isothiocyanato-1H-indole

Chemical Formula 25

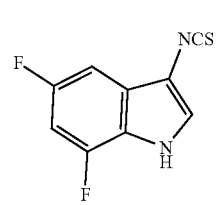

(Step 1) Production of N-(5,7-difluoro-1H-indol-3-yl)-2,2,2-trifluoroacetamide

Chemical Formula 26

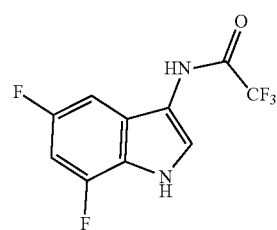

Trifluoroacetic anhydride (7.98 g, 38 mmol) was added dropwise to a THF solution (35 mL) of 2,2-diethoxyethane-1-amine (4.6 g, 34.5 mmol) and DIPEA (5.36 g, 41.4 mmol), and a residual reagent was added dropwise to a dropping funnel by putting THF (5 mL). After stirred at room temperature for 40 minutes, the reaction mixture was washed twice with a mixed solution of saturated saline (15 mL) and concentrated hydrochloric acid (1.15 mL), and the organic layer was distilled off under reduced pressure. The resulting residue (5.36 g) was dissolved in a mixed solvent of 1,2-dichloroethane/toluene (1:1, 40 mL), (2,4-difluorophenyl)hydrazine hydrochloride (5.2 g, 28.8 mmol) was added to this solution and stirred at 50° C. for 1.5 hours. The residue obtained by distilling the solvent off under reduced pressure was purified by amine-modified silica gel chromatography (hexane:ethyl acetate=1:0 to 7:3) to obtain the title compound (3.5 g). LCMS (m/z) 263.0 [M−H]−.

(Step 2) Production of 5,7-difluoro-1H-indol-3-amine Hydrochloride

Chemical Formula 27

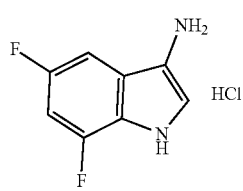

A mixture of N-(5,7-difluoro-1H-indol-3-yl)-2,2,2-trifluoroacetamide (3.5 g, 13.25 mmol) and 2N hydrochloric acid/ethanol solution (30 mL) was stirred at 80° C. overnight. The solvent was distilled off under reduced pressure, ethyl acetate was added to the resulting residue, and the solid was filtered off and dried to obtain the title compound (2.3 g). LCMS (m/z) 169.1 [M+H]+.

(Step 3) Production of 5,7-difluoro-3-isothiocyanato-1H-indole. To a THF solution (50 mL) of 5,7-difluoro-1H-indol-3-amine hydrochloride (2.3 g, 11.24 mmol), thiophosgene (1.42 g, 12.37 mmol) and DIPEA (2.91 g, 22.48 mmol) was added and stirred at room temperature for 30 minutes. The residue obtained by distilling the solvent off under reduced pressure was crudely purified by silica gel chromatography (chloroform:methanol=1:0 to 4:1). The resulting crude product was dissolved in ethyl acetate and washed with dilute hydrochloric acid and saturated saline in order, and then dried over anhydrous sodium sulfate. The solvent was distilled off under reduced pressure to obtain the title compound (2 g). LCMS (m/z) 209.1 [M−H]−.

Reference Example 7. Production of tert-butyl 2-[2-amino-4-(trifluoromethyl)phenyl]-1-ethylhydrazine-1-carboxylate Chemical Formula 28

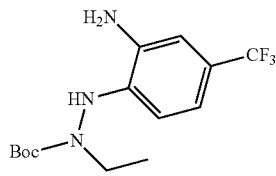

Production of tert-butyl 1-ethyl-2-[2-nitro-4-(trifluoromethyl)phenyl]hydrazine-1-carboxylate Chemical Formula 29

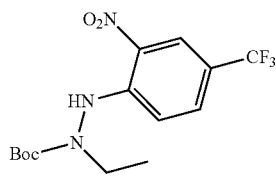

To a NMP solution (30 mL) of 1-fluoro-2-nitro-4-(trifluoromethyl)benzene (5.12 g, 24.49 mmol), tert-butyl 1-ethylhydrazine-1-carboxylate (5.1 g, 31.8 mmol) was added and stirred at 80° C. overnight. The reaction mixture was diluted with water and then extracted with ethyl acetate. The organic layer was washed with saturated saline and dried over anhydrous sodium sulfate, and then the solvent was distilled off under reduced pressure to obtain the title compound (8.5 g). LCMS (m/z) 348.3 [M−H]−.

(Step 2) Production of tert-butyl 2-[2-amino-4-(trifluoromethyl)phenyl]-1-ethylhydrazine-1-carboxylate. Tert-butyl 1-ethyl-2-[2-nitro-4-(trifluoromethyl)phenyl]hydrazine-1-carboxylate (8.5 g, 24.33 mmol) was dissolved in a mixed solvent of methanol/THF/saturated aqueous ammonium chloride solution (1:1:1, 180 mL), and zinc powder (7.95 g, 122 mmol) was added thereto at 0° C. and stirred at 0° C. for 25 minutes. The reaction mixture was filtered through Celite to remove insoluble materials. The organic layer was concentrated under reduced pressure, and the remaining aqueous layer was extracted with ethyl acetate, subsequently washed with saturated saline, and dried over anhydrous sodium sulfate. The residue obtained by distilling the solvent off under reduced pressure was purified by amine-modified silica gel chromatography (hexane:ethyl acetate=1:0-7:3) to obtain the title compound (7.0 g). ¹H NMR (DMSO-d₆) δ 7.53 (s, 1H), 6.86-6.84 (m, 1H), 6.82-6.76 (m, 1H), 6.50 (d, J=8.2 Hz, 1H), 5.04 (s, 2H), 3.47-3.36 (m, 2H), 1.35 (brs, 9H), 1.12 (t, J=7.1 Hz, 3H).

Example 1. Production of N2-(5-chloro-1H-indol-3-yl)-5-(trifluoromethyl)-1H-benzo[d]imidazol-1,2-diamine Hydrochloride Chemical Formula 30

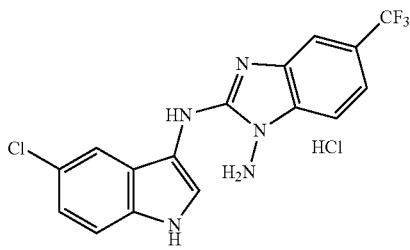

(Step 1) Production of tert-butyl {2-[(5-chloro-1H-indol-3-yl)amino]-5-(trifluoromethyl)-1H-benzo[d]imidazol-1-yl}carbamate Chemical Formula 31

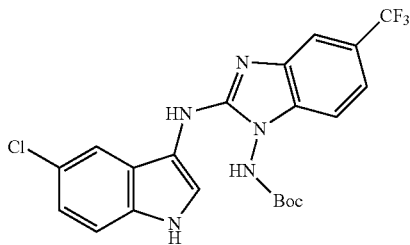

To a DMF solution (50 mL) of 5-chloro-3-isothiocyanato-1H-indole (Reference Example 1, 1.5 g, 7.19 mmol), tert-butyl 2-[2-amino-4-(trifluoromethyl)phenyl]hydrazine-1-carboxylate (Reference Example 2, 2.3 g, 7.91 mmol) was added and stirred at 50° C. overnight. After cooling the reaction mixture to room temperature, ethyl acetate was added and washed with water and saturated saline in order. The resulting organic layer was dried over anhydrous sodium sulfate, and the residue obtained by distilling the solvent off under reduced pressure was crudely purified by amine-modified silica gel chromatography (chloroform:methanol=1:0 to 19:1) to obtain thiourea (2.06 g). The resulting thiourea (2.06 g, 4.12 mmol) was dissolved in DMF (20 mL). To this solution, EDCI-HCl (1.19 g, 6.18 mmol) was added and stirred at 50° C. for 2.5 hours. After cooling the reaction mixture to room temperature, ethyl acetate was added and washed with water and saturated saline in order. The resulting organic layer was dried over anhydrous sodium sulfate, and the residue obtained by distilling the solvent off under reduced pressure was purified by silica gel chromatography (hexane:ethyl acetate=1:0 to 0:1) to obtain the title compound (1.89 g). LCMS (m/z) 466.2 [M+H]+.

(Step 2) Production of N2-(5-chloro-1H-indol-3-yl)-5-(trifluoromethyl)-1H-benzo[d]imidazol-1,2-diamine hydrochloride. A mixture of tert-butyl {2-[(5-chloro-1H-indol-3-yl)amino]-5-(trifluoromethyl)-1H-benzo[d]imidazol-1-yl}carbamate (1.89 g, 4.06 mmol) and 4N hydrochloric acid/ethyl acetate solution (25 mL) was stirred at room temperature for 2 hours. A precipitated solid was filtered off and dried to obtain the title compound (1.35 g). $^1$H NMR (Methanol-$d_4$) δ 7.72-7.66 (m, 2H), 7.62 (s, 1H), 7.57-7.54 (m, 2H), 7.50-7.47 (m, 1H), 7.22 (dd, J=8.8, 2.0 Hz, 1H); LCMS (m/z) 366.1 [M+H]+.

Example 2. Production of N2-(5,6-difluoro-1H-indol-3-yl)-5-(trifluoromethyl)-1H-benzo[d]imidazol-1,2-diamine Formate Chemical Formula 32

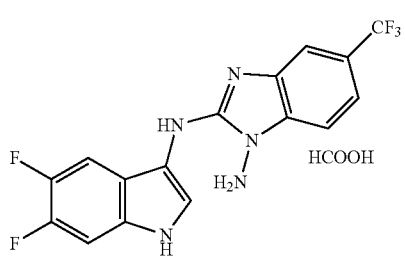

(Step 1) Production of tert-butyl {2-[(5,6-difluoro-1H-indol-3-yl)amino]-5-(trifluoromethyl)-1-benzo[d]imidazol-1-yl}carbamate Chemical Formula 33

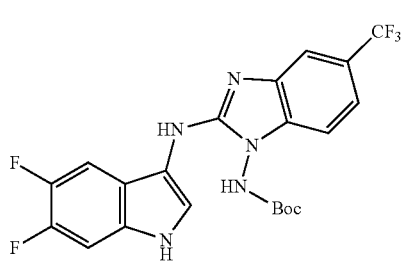

To a DMF solution (5 mL) of 5,6-difluoro-3-isothiocyanato-1H-indole (Reference Example 3, 150 mg, 0.714 mmol), tert-butyl 2-[2-amino-4-(trifluoromethyl)phenyl]hydrazine-1-carboxylate (Reference Example 2, 270 mg, 0.928 mmol) was added and stirred at 50° C. overnight. After cooling the reaction mixture to room temperature, ethyl acetate was added and washed with water and saturated saline in order. The organic layer was distilled off under reduced pressure, and the resulting residue was crudely purified by amine-modified silica gel chromatography (chloroform:methanol=1:0 to 19:1) to obtain thiourea (110 mg). The resulting thiourea (110 mg, 0.219 mmol) was dissolved in DMF (2 mL). To this solution, EDCI-HCl (63.1 mg, 0.329 mmol) was added and stirred at 50° C. for 3 hours. After cooling the reaction mixture to room temperature, ethyl acetate was added and washed with water and saturated saline in order. The organic layer was distilled off under reduced pressure, and the resulting residue was purified by silica gel chromatography (hexane:ethyl acetate=1:0 to 1:1) to obtain the title compound (55 mg). LCMS (m/z) 468.1 [M+H]+.

(Step 2) Production of N2-(5,6-difluoro-1H-indol-3-yl)-5-(trifluoromethyl)-1H-benzo[d]imidazol-1,2-diamine formate. A mixture of tert-butyl {2-[(5,6-difluoro-1H-indol-3-yl)amino]-5-(trifluoromethyl)-1-benzo[d]imidazol-1-yl}carboxylate (55 mg, 0.118 mmol) and 4N hydrochloric acid/ethyl acetate solution (1 mL) was stirred at room temperature for 6 hours. The solvent was distilled off under reduced pressure, and the resulting residue was purified using HPLC preparative chromatography to obtain the title compound. $^1$H NMR (DMSO-$d_6$) δ 11.03-10.98 (m, 1H), 8.77 (s, 1H), 8.25 (s, 1H), 7.89 (d, J=2.5 Hz, 1H), 7.80 (dd, J=11.7, 8.1 Hz), 7.52 (d, J=1.5 Hz, 1H), 7.41-7.31 (m, 3H), 5.91 (s, 2H); LCMS (m/z) 368.1 [M+H]+.

Example 3. Production of N2-(4,5-difluoro-1H-indol-3-yl)-N1-methyl-5-(trifluoromethyl)-1H-benzo[d]imidazol-1,2-diamine Hydrochloride Chemical Formula 34

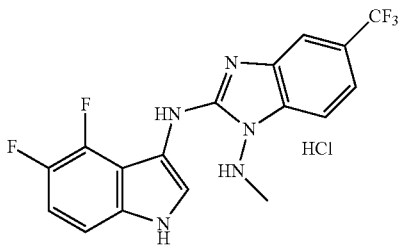

(Step 1) Production of tert-butyl {2-[(4,5-difluoro-1H-indol-3-yl)amino]-5-(trifluoromethyl)-1H-benzo[d]imidazole-1-yl}(methyl)carbamate Chemical Formula 35

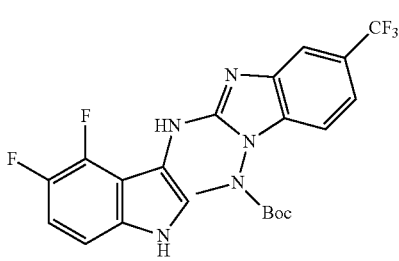

To a DMF solution (15 mL) of 4,5-difluoro-3-isothiocyanato-1H-indole (Reference Example 4, 1.35 g, 6.42 mmol), tert-butyl 2-[2-amino-4-(trifluoromethyl)phenyl]-1-methylhydrazine-1-carboxylate (Reference Example 5, 2.55 g, 8.35 mmol) was added and stirred at 60° C. for 5 hours. After cooling the reaction mixture to room temperature, it was diluted with water and extracted twice with ethyl acetate. The resulting organic layer was washed with water and saturated saline in order and dried over anhydrous sodium sulfate. The residue obtained by distilling the solvent off under reduced pressure was crudely purified by amine-modified silica gel chromatography (hexane:ethyl acetate=1:0 to 0:1, subsequently ethyl acetate:methanol=1:0 to 3:7) to obtain thiourea (2.52 g). The resulting thiourea (2.517 g, 4.88 mmol) was dissolved in DMF (20 mL). To this solution, EDCI-HCl (1.872 g, 9.77 mmol) and pyridine (0.772 g, 9.77 mmol) were added and stirred at 50° C. for 30 minutes. After cooling the reaction mixture to room temperature, it was diluted with water and extracted twice with ethyl acetate. The resulting organic layer was washed with water and saturated saline in order and dried over anhydrous sodium sulfate. The residue obtained by distilling the solvent off under reduced pressure was purified by silica gel chromatography (hexane:ethyl=1:0 to 0:1) to obtain the title compound (1.596 g). $^1$H NMR (Chloroform-d) δ 8.81 (s, 1H), 7.82-7.79 (m, 1H), 7.78-7.74 (m, 1H), 7.43-7.38 (m, 1H), 7.15-7.08 (m, 1H), 7.01-6.89 (m, 2H), 6.80-6.75 (m, 1H), 3.47 (s, 3H), 1.42 (s, 9H); LCMS (m/z) 482.2 [M+H]+.

(Step 2) Production of N2-(4,5-difluoro-1H-indol-3-yl)-N1-methyl-5-(trifluoromethyl)-1H-benzo[d]imidazol-1,2-diamine hydrochloride. A mixture of tert-butyl {2-[(4,5-difluoro-1H-indol-3-yl)amino]-5-(trifluoromethyl)-1H-benzo[d]imidazol-1-yl}(methyl)carbamate (1.595 g, 3.31 mmol) and 4N hydrochloric acid/ethyl acetate solution (10 mL) was stirred at room temperature for 2 hours. A precipitated solid was filtered off and dried to obtain the title compound (1.172 g). $^1$H NMR (Methanol-$d_4$) δ 7.74 (d, J=8.5 Hz, 1H), 7.68 (d, J=8.4 Hz, 1H), 7.63 (s, 1H), 7.60-7.57 (m, 1H), 7.29-7.24 (m, 1H), 7.19-7.08 (m, 1H), 3.02 (s, 3H); LCMS (m/z) 382.2 [M+H]+.

Example 4. Production of N2-(5,6-difluoro-1H-indol-3-yl)-N1-methyl-5-(trifluoromethyl)-1H-benzo[d]imidazol-1,2-diamine Chemical Formula 36

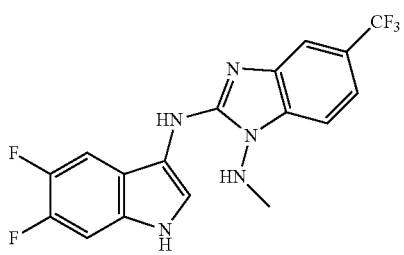

(Step 1) Production of tert-butyl {2-[(5,6-difluoro-1H-indol-3-yl)amino]-5-(trifluoromethyl)-1H-benzo[d]imidazol-1-yl}(methyl)carbamate Chemical Formula 37

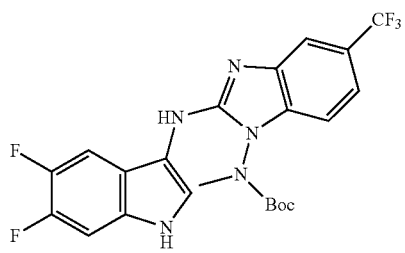

To a DMF solution (1 mL) of 5,6-difluoro-3-isothiocyanato-1H-indole (Reference Example 3, 103 mg, 0.491 mmol), tert-butyl 2-[2-amino-4-(trifluoromethyl)phenyl]-1-methylhydrazine-1-carboxylate (Reference Example 5, 125 mg, 0.409 mmol) was added and stirred at 50° C. for 1 hour, and then stirred at 70° C. for 2 hours. In order to complete the reaction, 5,6-difluoro-3-isothiocyanato-1H-indole (20 mg, 0.095 mmol) was put therein and further stirred at 70° C. for 30 minutes. After cooling the reaction mixture to room temperature, it was diluted with water and extracted twice with ethyl acetate. The resulting organic layer was washed with water and saturated saline in order and dried over anhydrous sodium sulfate. The residue obtained by distilling the solvent off under reduced pressure was crudely purified by amine-modified silica gel chromatography (hexane:ethyl acetate=1:0 to 0:1, subsequently ethyl acetate:methanol=1:0 to 3:7) to obtain thiourea (45 mg). The resulting thiourea (43 mg, 0.083 mmol) was dissolved in DMF (1 mL). To this solution, EDCI-HCl (32 mg, 0.167 mmol) and pyridine (13.2 mg, 0.167 mmol) were added and stirred at 50° C. for 1.5 hours. After cooling the reaction mixture to room temperature, it was diluted with water and extracted twice with ethyl acetate. The resulting organic layer was washed with water and saturated saline in order and dried over anhydrous sodium sulfate. The residue obtained by distilling the solvent off under reduced pressure was purified by silica gel chromatography (hexane:ethyl acetate=1:0 to 0:1) to obtain the title compound (21.6 mg). $^1$H NMR (Chloroform-d) δ 8.28 (brs, 1H), 7.74 (s, 1H), 7.69 (d, J=2.6 Hz, 1H), 7.41-7.37 (m, 1H), 7.25-7.22 (m, 1H), 7.15 (dd, J=10.3, 6.5 Hz, 1H), 7.10 (d, J=8.2 Hz, 1H), 6.26 (s, 1H), 3.47 (s, 3H), 1.41 (s, 9H); LCMS (m/z) 482.2 [M+H]+.

(Step 2) Production of N2-(5,6-difluoro-1H-indol-3-yl)-N1-methyl-5-(trifluoromethyl)-1H-benzo[d]imidazol-1,2-diamine. A mixture of tert-butyl {2-[(5,6-difluoro-1H-indol-3-yl)amino]-5-(trifluoromethyl)-1H-benzo[d]imidazol-1-yl}(methyl)carbamate (20.9 mg, 0.043 mmol) and 4N hydrochloric acid/ethyl acetate solution (1 mL) was stirred at room temperature for 2 hours. The reaction mixture was neutralized by adding saturated sodium bicarbonate and extracted with ethyl acetate. The resulting organic layer was washed with water and saturated saline in order, and dried over anhydrous sodium sulfate. The residue obtained by distilling the solvent off under reduced pressure was purified by silica gel chromatography (hexane:ethyl acetate=1:0 to 0:1, subsequently ethyl acetate:methanol=1:0 to 9:1) to obtain the title compound (13.2 mg). $^1$H NMR (DMSO-$d_6$) δ 11.05-11.00 (m, 1H), 8.77 (s, 1H), 7.87 (d, J=2.5 Hz, 1H), 7.78 (dd, J=11.7, 8.1 Hz, 1H), 7.55-7.53 (m, 1H), 7.44 (d, J=8.2 Hz, 1H), 7.42-7.31 (m, 2H), 6.60-6.51 (m, 1H), 2.81 (d, J=5.5 Hz, 3H); LCMS (m/z) 382.1 [M+H]+.

Example 5. Production of N2-(5,7-difluoro-1H-indol-3-yl)-N1-methyl-5-(trifluoromethyl)-1H-benzo[d]imidazol-1,2-diamine Chemical Formula 38

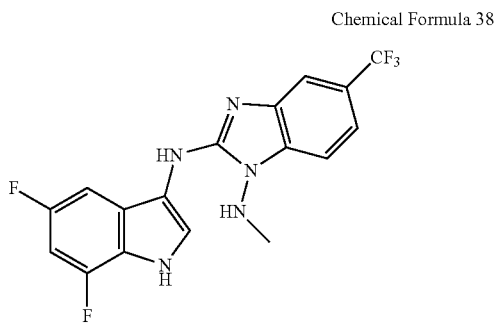 [SMILES: CNn1c(Nc2c[nH]c3c(F)cc(F)cc23)nc2cc(C(F)(F)F)ccc21]

(Step 1) Production of tert-butyl {2-[(5,7-difluoro-1H-indol-3-yl)amino]-5-(trifluoromethyl)-1H-benzo[d]imidazol-1-yl}(methyl)carbamate Chemical Formula 39

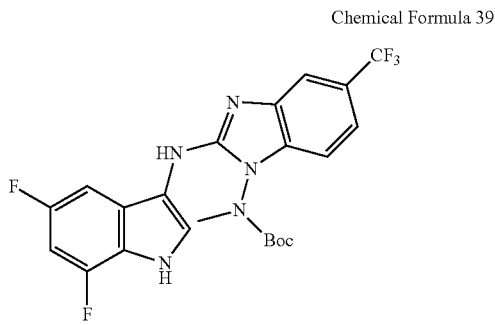 [SMILES: CN(C(=O)OC(C)(C)C)n1c(Nc2c[nH]c3c(F)cc(F)cc23)nc2cc(C(F)(F)F)ccc21]

To a DMF solution (2 mL) of 5,7-difluoro-3-isothiocyanato-1H-indole (Reference Example 6, 49.2 mg, 0.234 mmol), tert-butyl 2-[2-amino-4-(trifluoromethyl)phenyl]-1-methylhydrazine-1-carboxylate (Reference Example 5, 55 mg, 0.18 mmol) was added and stirred at 50° C. overnight. After cooling the reaction mixture to room temperature, ethyl acetate was added and washed with water and saturated saline in order. The organic layer was dried over anhydrous sodium sulfate, and then the residue obtained by distilling the solvent off under reduced pressure was crudely purified by amine-modified silica gel chromatography (chloroform:methanol=1:0 to 1:1) to obtain thiourea (34 mg). The resulting thiourea (34 mg, 0.066 mmol) was dissolved in DMF (0.7 mL). To this solution, EDCI-HCl (18.97 mg, 0.099 mmol) was added and stirred at 50° C. for 2 hours. After cooling the reaction mixture to room temperature, ethyl acetate was added and washed with water and saturated saline in order. The organic layer was dried over anhydrous sodium sulfate, and then the residue obtained by distilling the solvent off under reduced pressure was purified by silica gel chromatography (hexane:ethyl acetate=1:0 to 1:1) to obtain the title compound (18.7 mg). LCMS (m/z) 482.2 [M+H]+.

(Step 2) Production of N2-(5,7-difluoro-1H-indol-3-yl)-N1-methyl-5-(trifluoromethyl)-1H-benzo[d]imidazol-1,2-diamine. A mixture of tert-butyl {2-[(5,7-difluoro-1H-indol-3-yl)amino]-5-(trifluoromethyl)-1H-benzo[d]imidazol-1-yl}(methyl)carbamate (18.7 mg, 0.039 mmol) and 4N hydrochloric acid/ethyl acetate solution (1 mL) was stirred at room temperature for 1 hour. The reaction mixture was neutralized by adding saturated sodium bicarbonate and extracted with ethyl acetate. The organic layer was washed with water and saturated saline in order and dried over anhydrous sodium sulfate. The residue obtained by distilling the solvent off under reduced pressure was purified by silica gel chromatography (hexane:ethyl acetate=1:0 to 0:1) to obtain the title compound (10.3 mg). $^1$H NMR (DMSO-$d_6$) δ 11.52-11.48 (m, 1H), 8.80 (s, 1H), 7.93 (d, J=2.6 Hz, 1H), 7.58-7.54 (m, 1H), 7.48-7.40 (m, 2H), 7.37-7.32 (m, 1H), 7.05-6.95 (m, 1H), 6.60-6.53 (m, 1H), 2.81 (d, J=5.5 Hz, 3H); LCMS (m/z) 382.1 [M+H]+.

Example 6. Production of N2-(5-chloro-1H-indol-3-yl)-N1-ethyl-5-(trifluoromethyl)-1H-benzo[d]imidazol-1,2-diamine Hydrochloride Chemical Formula 40

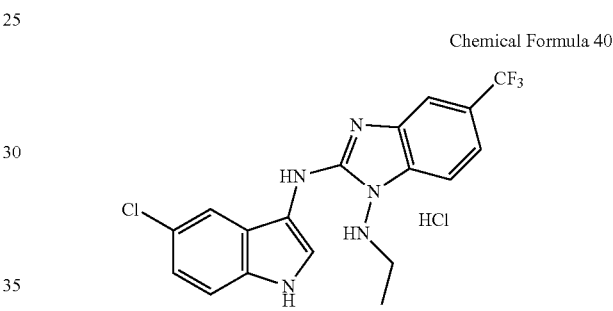

(Step 1) Production of tert-butyl {2-[(5-chloro-1H-indol-3-yl)amino]-5-(trifluoromethyl)-1H-benzo[d]imidazol-1-yl}(ethyl)carbamate Chemical Formula 41

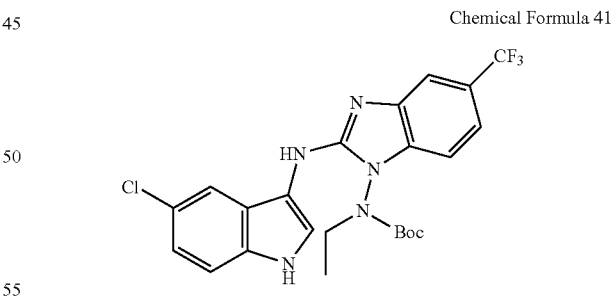

To a DMF solution (30 mL) of 5-chloro-3-isothiocyanato-1H-indole (Reference Example 1, 1.2 g, 5.75 mmol), tert-butyl 2-[2-amino-4-(trifluoromethyl)phenyl]-1-ethylhydrazine-1-carboxylate (Reference Example 7, 2.02 g, 6.33 mmol) was added and stirred at 50° C. overnight. After cooling the reaction mixture to room temperature, ethyl acetate was added and washed with water and saturated saline in order. The organic layer was dried over anhydrous sodium sulfate, and the residue obtained by distilling the solvent off under reduced pressure was crudely purified by amine-modified silica gel chromatography (chloroform:

methanol=1:0 to 97:3) to obtain thiourea (1.7 g). The resulting thiourea (1.7 g, 3.22 mmol) was dissolved in DMF (20 mL). To this solution, EDCI-HCl (0.926 g, 4.83 mmol) was added and stirred at 55° C. for 1 hour. After cooling the reaction mixture to room temperature, ethyl acetate was added and washed with water and saturated saline in order. The organic layer was dried over anhydrous sodium sulfate, and the residue obtained by distilling the solvent off under reduced pressure was purified by silica gel chromatography (hexane:ethyl acetate=1:0 to 7:3) to obtain the title compound (1.38 g). LCMS (m/z) 494.2 [M+H]+.

(Step 2) Production of N2-(5-chloro-1H-indol-3-yl)-N1-ethyl-5-(trifluoromethyl)-1H-benzo[d]imidazol-1,2-diamine hydrochloride. A mixture of tert-butyl {2-[(5-chloro-1H-indol-3-yl)amino]-5-(trifluoromethyl)-1H-benzo[d]imidazol-1-yl}(ethyl)carbamate (1.38 g, 2.79 mmol) and 4N hydrochloric acid/ethyl acetate solution (20 mL) was stirred at 55° C. for 45 minutes. A precipitated solid was filtered off and dried to obtain the title compound (677 mg). $^1$H NMR (Methanol-$d_4$) δ 7.74 (d, J=8.4 Hz, 1H), 7.70-7.66 (m, 1H), 7.63 (s, 1H), 7.58-7.55 (m, 1H), 7.53-7.51 (m, 1H), 7.50-7.47 (m, 1H), 7.23 (dd, J=8.7, 2.0 Hz, 1H), 3.40 (q, J=7.2 Hz, 2H), 1.31 (t, J=7.2 Hz, 3H); LCMS (m/z) 394.1 [M+H]+.

Examples 7 to 29

The following Example compounds Table 1 were produced by using the corresponding raw materials (commercial products or compounds derivatized from commercial compounds by known methods or methods similar thereto) in accordance with the methods described in Examples above, and, if necessary, by combining methods normally used in organic synthetic chemistry as appropriate. The physicochemical data of each compound is shown in Table 2.

TABLE 1

| Example | Structure | Name |
|---|---|---|
| 7 | 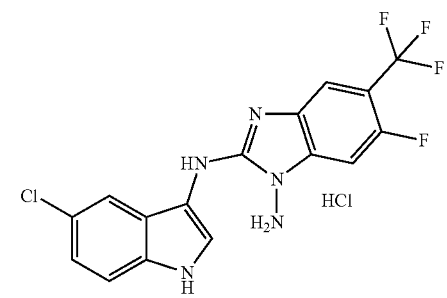 [SMILES: Nn1c(Nc2c[nH]c3ccc(Cl)cc23)nc2cc(C(F)(F)F)c(F)cc21 ; Cl] | N2-(5-chloro-1H-indol-3-yl)-6-fluoro-5-(trifluoromethyl)-1H-benzo[d]imidazole-1,2-diamine hydrochloride |
| 8 | 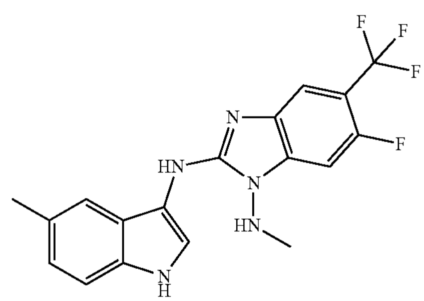 [SMILES: CNn1c(Nc2c[nH]c3ccc(C)cc23)nc2cc(C(F)(F)F)c(F)cc21] | 6-fluoro-N1-methyl-N2-(5-methyl-1H-indol-3-yl)-5-(trifluoromethyl)-1H-benzo[d]imidazole-1,2-diamine |
| 9 | 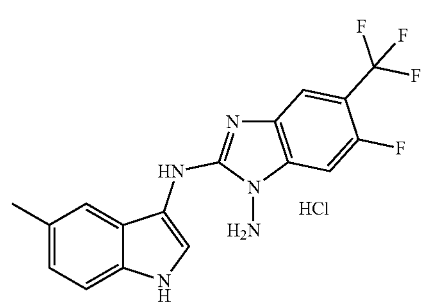 [SMILES: Cc1ccc2[nH]cc(Nc3nc4cc(C(F)(F)F)c(F)cc4n3N)c2c1 ; Cl] | 6-fluoro-N2-(5-methyl-1H-indol-3-yl)-5-(trifluoromethyl)-1H-benzo[d]imidazole-1,2-diamine hydrochloride |

TABLE 1-continued

| Example | Structure | Name |
|---|---|---|
| 10 | 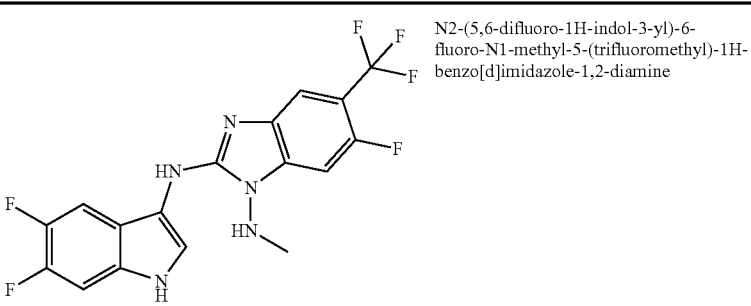 | N2-(5,6-difluoro-1H-indol-3-yl)-6-fluoro-N1-methyl-5-(trifluoromethyl)-1H-benzo[d]imidazole-1,2-diamine |
| 11 | 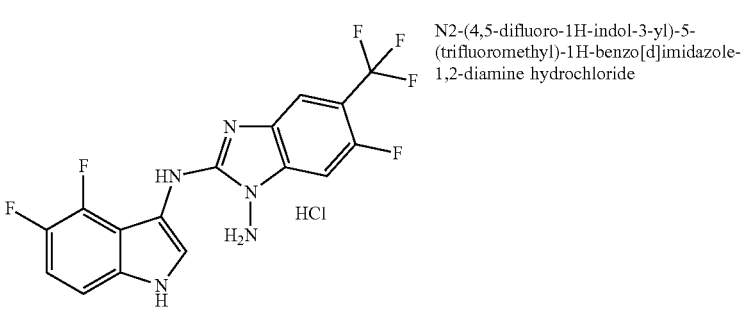 | N2-(4,5-difluoro-1H-indol-3-yl)-5-(trifluoromethyl)-1H-benzo[d]imidazole-1,2-diamine hydrochloride |
| 12 | 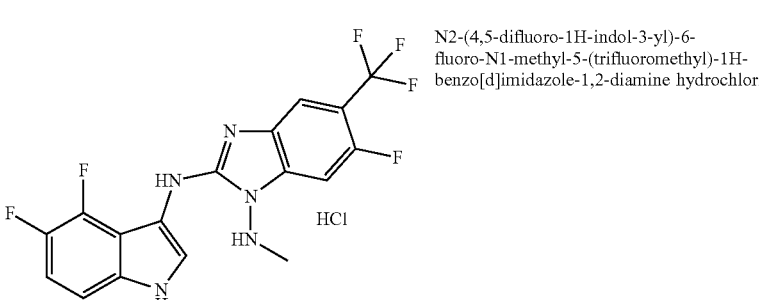 | N2-(4,5-difluoro-1H-indol-3-yl)-6-fluoro-N1-methyl-5-(trifluoromethyl)-1H-benzo[d]imidazole-1,2-diamine hydrochloride |
| 13 | 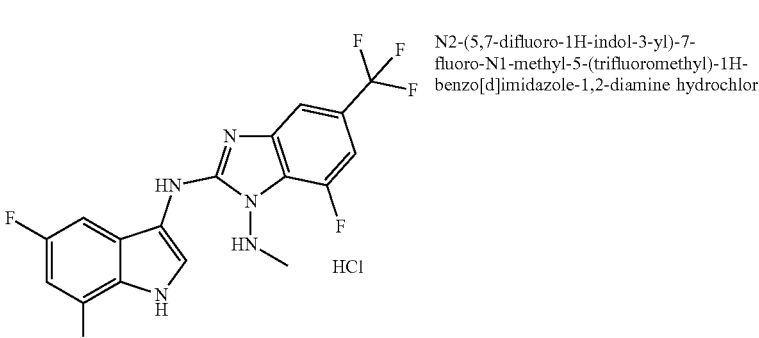 | N2-(5,7-difluoro-1H-indol-3-yl)-7-fluoro-N1-methyl-5-(trifluoromethyl)-1H-benzo[d]imidazole-1,2-diamine hydrochloride |
| 14 | 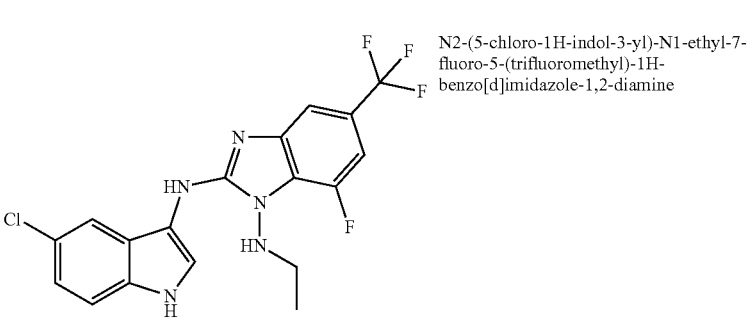 | N2-(5-chloro-1H-indol-3-yl)-N1-ethyl-7-fluoro-5-(trifluoromethyl)-1H-benzo[d]imidazole-1,2-diamine |

TABLE 1-continued

| Example | Structure | Name |
|---|---|---|
| 15 | 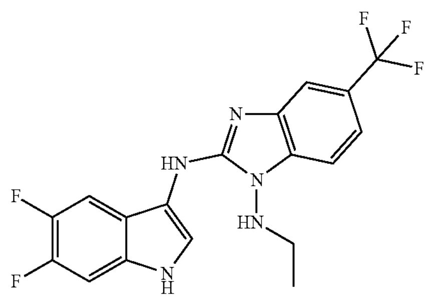 [SMILES: CCNn1c(Nc2c[nH]c3cc(F)c(F)cc23)nc2cc(C(F)(F)F)ccc21] | N2-(5,6-difluoro-1H-indol-3-yl)-N1-ethyl-5-(trifluoromethyl)-1H-benzo[d]imidazole-1,2-diamine |
| 16 | 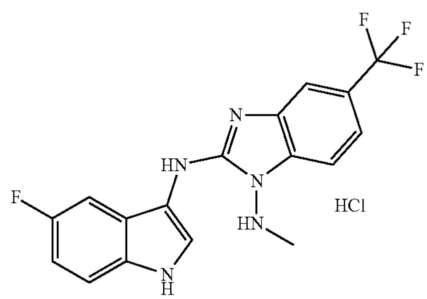 [SMILES: CNn1c(Nc2c[nH]c3ccc(F)cc23)nc2cc(C(F)(F)F)ccc21 ; Cl] | N2-(5-fluoro-1H-indol-3-yl)-N1-methyl-5-(trifluoromethyl)-1H-benzo[d]imidazole-1,2-diamine hydrochloride |
| 17 | 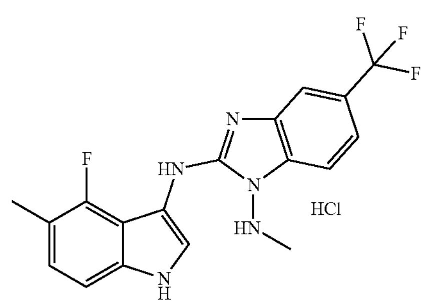 [SMILES: CNn1c(Nc2c[nH]c3ccc(C)c(F)c23)nc2cc(C(F)(F)F)ccc21 ; Cl] | N2-(4-fluoro-5-methyl-1H-indol-3-yl)-N1-methyl-5-(trifluoromethyl)-1H-benzo[d]imidazole-1,2-diamine hydrochloride |
| 18 | 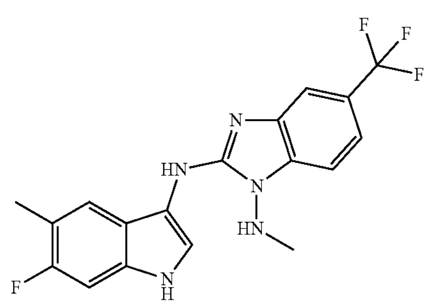 [SMILES: CNn1c(Nc2c[nH]c3cc(F)c(C)cc23)nc2cc(C(F)(F)F)ccc21] | N2-(6-fluoro-5-methyl-1H-indol-3-yl)-N1-methyl-5-(trifluoromethyl)-1H-benzo[d]imidazole-1,2-diamine |
| 19 | 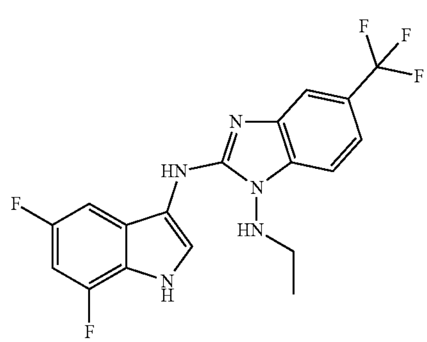 [SMILES: CCNn1c(Nc2c[nH]c3c(F)cc(F)cc23)nc2cc(C(F)(F)F)ccc21] | N2-(5,7-difluoro-1H-indol-3-yl)-N1-ethyl-5-(trifluoromethyl)-1H-benzo[d]imidazole-1,2-diamine |

TABLE 1-continued

| Example | Structure | Name |
|---|---|---|
| 20 | 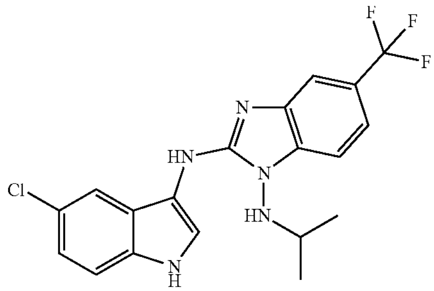 [SMILES: CC(C)Nn1c(Nc2c[nH]c3ccc(Cl)cc23)nc2cc(C(F)(F)F)ccc21] | N2-(5-chloro-1H-indol-3-yl)-N1-isopropyl-5-(trifluoromethyl)-1H-benzo[d]imidazole-1,2-diamine |
| 21 | 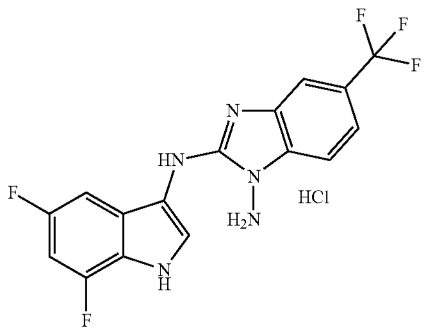 [SMILES: Nn1c(Nc2c[nH]c3c(F)cc(F)cc23)nc2cc(C(F)(F)F)ccc21 ; Cl] | N2-(5,7-difluoro-1H-indol-3-yl)-5-(trifluoromethyl)-1H-benzo[d]imidazole-1,2-diamine hydrochloride |
| 22 | 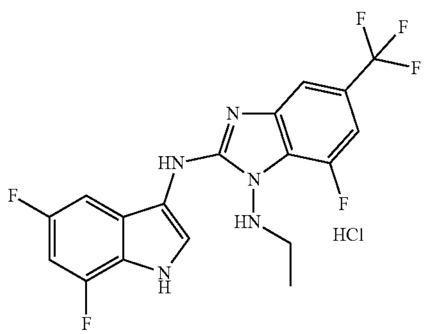 [SMILES: CCNn1c(Nc2c[nH]c3c(F)cc(F)cc23)nc2cc(C(F)(F)F)cc(F)c21 ; Cl] | N2-(5,7-difluoro-1H-indol-3-yl)-N1-ethyl-7-fluoro-5-(trifluoromethyl)-1H-benzo[d]imidazole-1,2-diamine hydrochloride |
| 23 | 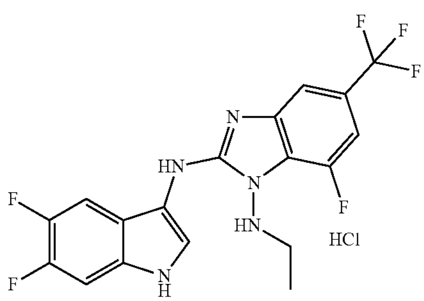 [SMILES: CCNn1c(Nc2c[nH]c3cc(F)c(F)cc23)nc2cc(C(F)(F)F)cc(F)c21 ; Cl] | N2-(5,6-difluoro-1H-indol-3-yl)-N1-ethyl-7-fluoro-5-(trifluoromethyl)-1H-benzo[d]imidazole-1,2-diamine hydrochloride |
| 24 | 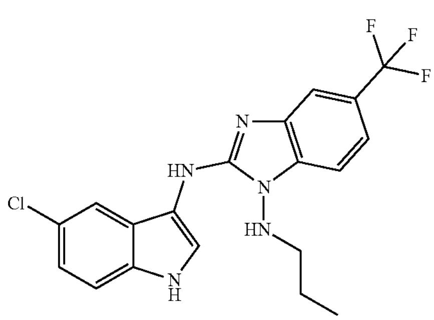 [SMILES: CCCNn1c(Nc2c[nH]c3ccc(Cl)cc23)nc2cc(C(F)(F)F)ccc21] | N2-(5-chloro-1H-indol-3-yl)-N1-propyl-5-(trifluoromethyl)-1H-benzo[d]imidazole-1,2-diamine |

TABLE 1-continued

| Example | Structure | Name |
|---|---|---|
| 25 | 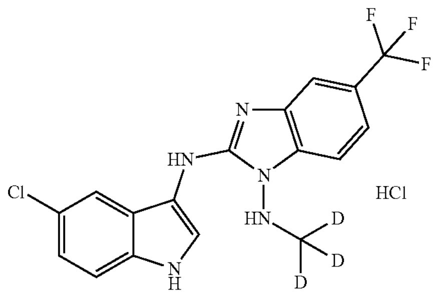 [SMILES: [2H]C([2H])([2H])Nn1c(Nc2c[nH]c3ccc(Cl)cc23)nc2cc(C(F)(F)F)ccc21 ; Cl] | N2-(5-chloro-1H-indol-3-yl)-N1-(methyl-d3)-5-(trifluoromethyl)-1H-benzo[d]imidazole-1,2-diamine hydrochloride |
| 26 | 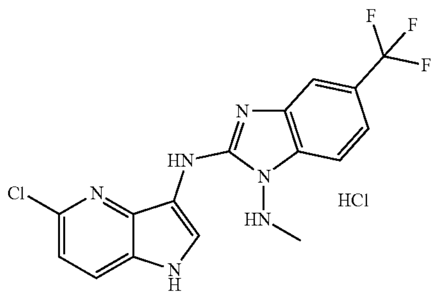 [SMILES: CNn1c(Nc2c[nH]c3ccc(Cl)nc23)nc2cc(C(F)(F)F)ccc21 ; Cl] | N2-(5-chloro-1H-pyrrolo[3,2-b]pyridin-3-yl)-N1-methyl-5-(trifluoromethyl)-1H-benzo[d]imidazole-1,2-diamine hydrochloride |
| 27 | 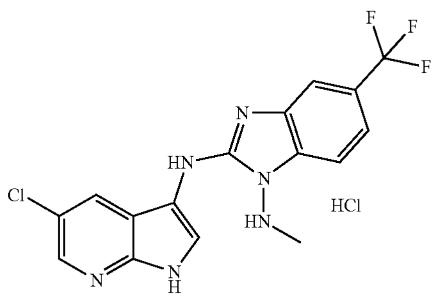 [SMILES: CNn1c(Nc2c[nH]c3ncc(Cl)cc23)nc2cc(C(F)(F)F)ccc21 ; Cl] | N2-(5-chloro-1H-pyrrolo[2,3-b]pyridin-3-yl)-N1-methyl-5-(trifluoromethyl)-1H-benzo[d]imidazole-1,2-diamine hydrochloride |
| 28 | 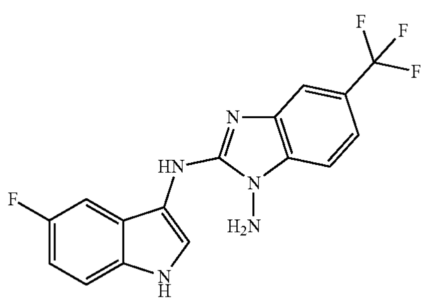 [SMILES: Nn1c(Nc2c[nH]c3ccc(F)cc23)nc2cc(C(F)(F)F)ccc21] | N2-(5-fluoro-1H-indol-3-yl)-5-(trifluoromethyl)-1H-benzo[d]imidazole-1,2-diamine |
| 29 | 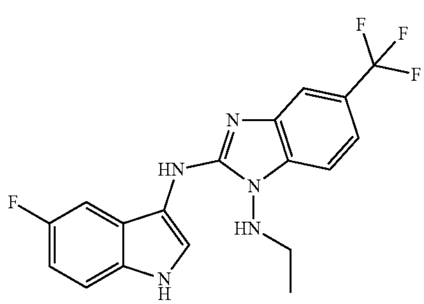 [SMILES: CCNn1c(Nc2c[nH]c3ccc(F)cc23)nc2cc(C(F)(F)F)ccc21] | N1-ethyl-N2-(5-fluoro-1H-indol-3-yl)-5-(trifluoromethyl)-1H-benzo[d]imidazole-1,2-diamine |

TABLE 2

| Example | ¹H NMR δ (ppm) | LCMS m/z [M + H]+ |
|---|---|---|
| 7 | (Methanol-d₄) δ 7.60 (s, 1H), 7.56-7.54 (m, 1H), 7.52-7.42 (m, 3H), 7.21 (dd, J = 8.7, 2.0 Hz, 1H). | 384.1 |
| 8 | (DMSO-d₆) δ 10.75-10.70 (m, 1H), 8.59 (s, 1H), 7.71 (d, J = 2.5 Hz, 1H), 7.52-7.45 (m, 2H), 7.35 (d, J = 10.7 Hz, 1H), 7.26 (d, J = 8.3 Hz, 1H), 6.96-6.91 (m, 1H), 6.53 (q, J = 5.4 Hz, 1H), 2.81 (d, J = 5.5 Hz, 3H), 2.39 (s, 3H). | 378.1 |
| 9 | (Methanol-d₄) δ 7.48-7.41 (m, 2H), 7.39-7.28 (m, 3H), 7.05-7.01 (m, 1H), 2.41 (s, 3H). | 364.2 |
| 10 | (DMSO-d₆) δ 11.08-11.01 (m, 1H), 8.84 (brs, 1H), 7.84 (d, J = 2.5 Hz, ¹H), 7.77 (dd, J = 11.7, 8.1Hz, 1H), 7.51 (d, J = 6.2 Hz, 1H), 7.43-7.33 (m, 2H), 6.58-6.49 (m, 1H), 2.83-2.79 (m, 3H). | 400.1 |
| 11 | (Methanol-d₄) δ 7.68-7.63 (m, 2H), 7.62 (s, 1H), 7.57-7.55 (m, 1H), 7.28-7.23 (m, 1H), 7.19-7.07 (m, 1H). | 368.1 |
| 12 | (Methanol-d4) δ 7.70-7.61 (m, 2H), 7.55 (d, J = 5.6 Hz, 1H), 7.29-7.24 (m, 1H), 7.20-7.09 (m, 1H), 3.01 (s, 3H). | 400.1 |
| 13 | (Methanol-d₄) δ 7.68 (s, 1H), 7.52-7.46 (m, 1H), 7.41-7.38 (m, 1H), 7.12 (dd, J = 9.0, 2.2 Hz, 1H), 6.94-6.84 (m, 1H), 3.07-3.03 (m, 3H). | 400.1 |
| 14 | (DMSO-d₆) δ 11.14-11.10 (m, 1H), 8.79 (s, 1H), 7.79 (d, J = 2.5 Hz, 1H), 7.74 (d, J = 2.1 Hz, 1H), 7.43-7.38 (m, 2H), 7.24-7.19 (m, 1H), 7.10 (dd, J = 8.6, 2.1 Hz, 1H), 6.61 (t, J = 4.2 Hz, 1H), 3.23-3.13 (m, 2H), 1.12 (t, J = 7.2 Hz, 3H). | 412.1 |
| 15 | (DMSO-d₆) δ 11.06-11.01 (m, 1H), 8.69 (s, 1H), 7.84 (d, J = 2.5 Hz, 1H), 7.71 (dd, J = 11.6, 8.1Hz, 1H), 7.55-7.51 (m, 1H), 7.43 (d, J = 8.2 Hz, 1H), 7.38 (dd, J= 11.3, 6.9Hz, 1H), 7.35-7.30 (m, 1H), 6.65 (t, J = 4.4 Hz, 1H), 3.20-3.11 (m, 2H), 1.09 (t, J = 7.1 Hz, 3H). | 396.2 |
| 16 | (Methanol-d₄) δ 7.74 (d, J = 8.4 Hz, 1H), 7.71-7.65 (m, 1H), 7.63 (s, 1H), 7.57-7.55 (m, 1H), 7.47 (dd, J = 8.9, 4.2 Hz, 1H), 7.24 (dd, J = 9.3, 2.5 Hz, 1H), 7.03 (td, J = 9.1, 2.5 Hz, 1H), 3.05 (s, 3H). | 364.1 |
| 17 | (Methanol-d₄) δ 7.77 (d, J = 8.5 Hz, 1H), 7.74-7.69 (m, 1H), 7.59-7.56 (m, 1H), 7.52-7.50 (m, 1H), 7.21 (d, J = 8.4 Hz, 1H), 7.09-7.04 (m, 1H), 3.03 (s, 3H), 2.28 (d, J = 2.2 Hz, 3H). | 378.2 |
| 18 | (DMSO-d₆) δ 10.80-10.76 (m, 1H), 8.62 (s, 1H), 7.74 (d, J = 2.4 Hz, 1H), 7.58 (d, J = 7.7 Hz, 1H), 7.54-7.52 (m, 1H), 7.43 (d, J = 8.2 Hz, 1H), 7.36-7.31 (m, 1H), 7.11 (d, J = 10.8 Hz, 1H), 6.56 (q, J = 5.4 Hz, 1H), 2.81 (d, J = 5.4 Hz, 3H), 2.32-2.29 (m, 3H). | 378.2 |
| 19 | (DMSO-d₆) δ 11.54-11.49 (m, 1H), 8.72 (s, 1H), 7.90 (d, J = 2.5 Hz, 1H), 7.56-7.53 (m, 1H), 7.43 (d, J = 8.2 Hz, 1H), 7.37 (dd, J = 9.7, 2.3 Hz, 1H), 7.35-7.31 (m, 1H), 7.04-6.96 (m, 1H), 6.66 (t, J = 4.5 Hz, 1H), 3.20-3.12 (m, 2H), 1.09 (t, J = 7.1 Hz, 3H). | 396.2 |
| 20 | (DMSO-d₆) δ 11.11-11.07 (m, 1H), 8.57 (s, 1H), 7.81 (d, J = 2.6 Hz, 1H), 7.71 (d, J = 2.0 Hz, 1H), 7.53-7.51 (m, 1H), 7.45-7.37 (m, 2H), 7.33-7.29 (m, 1H), 7.10 (dd, J = 8.7, 2.1 Hz, 1H), 6.59 (d, J = 2.1 Hz, 1H), 3.71-3.61 (m, 1H), 1.10-1.06 (m, 6H). | 408.2 |
| 21 | (Methanol-d₄) δ 7.70-7.61 (m, 3H), 7.54-7.52 (m, 1H), 7.10 (dd, J = 8.9, 2.1 Hz, 1H), 6.94-6.84 (m, 1H). | 368.1 |
| 22 | (Methanol-d₄) δ 7.68 (s, 1H), 7.52-7.46 (m, 1H), 7.41-7.38 (m, 1H), 7.07 (dd, J = 8.8, 2.2 Hz, 1H), 6.95-6.84 (m, 1H), 3.41-3.33 (m, 2H), 1.30 (t, J = 7.2 Hz, 3H). | 414.2 |
| 23 | (Methanol-d₄) δ 7.64-7.62 (m, 1H), 7.57-7.52 (m, 1H), 7.43-7.34 (m, 3H), 3.40-3.33 (m, 2H), 1.32 (t, J = 7.2 Hz, 3H). | 414.1 |
| 24 | (Methanol-d₄) δ 7.54 (s, 1H), 7.51-7.46 (m, 3H), 7.43-7.36 (m, 2H), 7.13 (dd, J = 8.7, 2.0 Hz, 1H), 3.29-3.20 (m, 2H), 1.73-1.60 (m, 2H), 1.06 (t, J = 7.4 Hz, 3H). | 408.2 |
| 25 | (Methanol-d₄) δ 7.75 (d, J = 8.4 Hz, 1H), 7.71-7.67 (m, 1H), 7.65-7.62 (m, 1H), 7.58-7.55 (m, 2H), 7.48 (dd, J = 8.7, 0.6 Hz, 1H), 7.23 (dd, J = 8.7, 2.0 Hz, 1H). | 383.1 |
| 26 | (Methanol-d₄) δ 7.99 (d, J = 8.6 Hz, 1H), 7.93 (s, 1H), 7.81-7.77 (m, 1H), 7.75-7.69 (m, 1H), 7.58-7.55 (m, 1H), 7.34 (d, J = 8.6 Hz, 1H), 3.08 (s, 3H). | 381.1 |
| 27 | (Methanol-d₄) δ 8.37-8.32 (m, 1H), 8.14-8.06 (m, 1H), 7.88-7.69 (m, 3H), 7.64-7.54 (m, 1H), 3.06 (s, 3H). | 381.1 |
| 28 | (DMSO-d₆) δ 10.95 (s, 1H), 8.65 (s, 1H), 7.88 (d, J = 2.6 Hz, 1H), 7.56-7.48 (m, 2H), 7.41-7.29 (m, 3H), 6.95 (td, J = 9.2, 2.6 Hz, 1H), 5.90 (s, 2H). | 350.1 |
| 29 | (DMSO-d₆) δ 10.99 (s, 1H), 8.60 (s, 1H), 7.81 (d, J = 2.6 Hz, 1H), 7.51 (d, J = 1.7 Hz, 1H), 7.47-7.30 (m, 3H), 7.26-7.08 (m, 1H), 7.00-6.92 (m, 1H), 6.65 (s, 1H), 3.22-3.13 (m, 2H), 1.11 (t, J = 7.1 Hz, 3H). | 378.2 |

Test Example 1. Inhibition Test of Intracellular Human STING (hSTING) Pathways Using Reporter Cells Since STING activates the transcription factor IRF3 by ligand stimulation, the activity of STING can be evaluated by a reporter assay using a secreted alkaline phosphatase (SEAP reporter) incorporated downstream of the IRF-inducible promoter. In other words, the hSTING inhibitory activity of the test compounds was evaluated using HEK-Blue™ ISG cells (manufactured by InvivoGen, #hkb-isg-1) into which the SEAP reporter was incorporated. The activation of hSTING was performed by stimulation with the small molecule ligand, Compound 3 as described in the literature (Ramanjulu, J. M., et al., Nature. 2018, 564 (7736), 439-443).

The HEK-Blue™ ISG cells were seeded in 96-well plates and cultured overnight at 37° C. in a 5% $CO_2$ incubator. To each well of the cell culture plates, a test compound solution adjusted to have a final concentration of 0.1 to 10 µM was added and cultured in the $CO_2$ incubator for 1 hour. Then, the Compound 3 (final concentration of 10 nM) was added thereto and further cultured in the $CO_2$ incubator for 21 hours. After collecting the culture supernatant from each well, the reporter activity was measured by luminous reaction of alkaline phosphatase.

Method for Evaluating Inhibitory Activity. Taking the reporter activity in the group without test compounds added and with Compound 3 added as 100% and the reporter activity in the group without test compounds added and without Compound 3 added as 0%, $IC_{50}$ values were determined by regression analysis of the inhibition rate calculated from the reporter activity at each compound concentration and the test compound concentration (logarithm).

Evaluation Result. Table 3 shows the inhibitory activity of representative compounds of the present invention on hSTING. The inhibitory effect on the hSTING was indicated by marking an $IC_{50}$ value of less than 0.1 µM with *, that of 0.1 µM or more and less than 1 µM with , that of 1 µM or more and less than 10 µM with *, and that of 10 µM or more with "-".

TABLE 3

| Test Compound (Example No.) | Inhibitory Activity on hSTING |
|---|---|
| 1 | *** |
| 2 | *** |
| 3 | *** |
| 4 | *** |
| 5 | *** |
| 6 | *** |
| 7 | *** |
| 8 | *** |
| 9 | ** |
| 10 | ** |
| 11 | ** |
| 12 | * |
| 13 | *** |
| 14 | *** |
| 15 | *** |
| 16 | *** |
| 17 | *** |
| 18 | *** |
| 19 | *** |
| 20 | * * |
| 21 | *** |
| 22 | *** |
| 23 | *** |

TABLE 3-continued

| Test Compound (Example No.) | Inhibitory Activity on hSTING |
|---|---|
| 24 | *** |
| 25 | *** |
| 26 | * |
| 27 | ** |
| 28 | ** |
| 29 | *** |

This result indicates that the compounds of formula (I) of the present invention have a strong inhibitory activity on the STING pathway.

Test Example 2. Inhibition Test of Human IFN-β Production by cGAMP Stimulation The human monocytic cell line THP-1 cells were used to measure the amount of IFN-β produced when stimulated with the endogenous ligand cGAMP, thereby evaluating the inhibitory activity of the test compounds on STING activation.

After THP-1 cells (manufactured by ATCC) were seeded in 96-well plates, PMA (manufactured by Santa Cruz Biotechnology, Inc.) adjusted to a concentration after addition of 100 nM was added and cultured overnight at a 37° C. in a 5% $CO_2$ incubator (10% FBS, 50 U/mL penicillin/50 µg/mL streptomycin-containing RPMI 1640 medium). To each well of the plate, a test compound solution adjusted to a final concentration of 0.001-1 µM of the test compound was added and cultured in the $CO_2$ incubator for 1 hour (DMSO final concentration of 0.1%). 0.12 µg/well of 2'3'-cGAMP (manufactured by ChemieTek, #CT-CGAMP) was introduced into the cells by transfection method using Lipofectamine 2000 (manufactured by Invitrogen) and cultured in the $CO_2$ incubator for another 18 hours. After collecting the culture supernatant from each well, the amount of human IFN-P production in the culture supernatant was measured by ELISA method using R&D human IFN-β Duoset (manufactured by R&D systems).

Method for Evaluating Inhibitory Activity. Taking the amount of human IFN-β production in the group without test compounds added and with cGAMP added as 100% and the amount of human IFN-β production in the group without test compounds added and without cGAMP added as 0%, $IC_{50}$ values were determined by regression analysis of the inhibition rate calculated from the amount of human IFN-β production at each compound concentration and the test compound concentration (logarithm).

Evaluation Result. Table 4 shows the inhibitory activity of representative compounds of the present invention on IFN-β production. The inhibitory effect on the IFN-β production was indicated by marking an $IC_{50}$ value of less than 0.01 µM with *, that of 0.01 µM or more and less than 0.1 µM with , that of 0.1 µM or more and less than 1 µM with *, and that of 1 µM or more with "-", and NT was marked as unmeasured.

TABLE 4

| Test Compound (Example No.) | Inhibitory effect on the IFN-β production |
|---|---|
| 1 | *** |
| 2 | *** |
| 3 | *** |

TABLE 4-continued

| Test Compound (Example No.) | Inhibitory effect on the IFN-β production |
|---|---|
| 4 | *** |
| 5 | *** |
| 6 | *** |
| 7 | *** |
| 8 | *** |
| 9 | *** |
| 10 | ** |
| 11 | ** |
| 12 | — |
| 13 | *** |
| 14 | *** |
| 15 | *** |
| 16 | *** |
| 17 | *** |
| 18 | *** |
| 19 | *** |
| 21 | * |
| 22 | ** |
| 23 | ** |
| 24 | ** |
| 25 | *** |
| 26 | * |
| 27 | * |
| 28 | ** |
| 29 | ** |

This result indicates that the compounds of formula (I) of the present invention have a strong suppressing effect on the production of IFN-β induced by the activation of STING in cells.

Test Example 3. Inhibition Test of Cytokine Production Using STING Agonist-Stimulated Mouse Models A mouse-STING agonist, CMA (10-Carboxymethyl-9-acridinone) was administered to mice to stimulate STING pathways, and then a suppressing effect of the compounds of formula (I) of the present invention on the production amount of cytokines (IFN-β and IL-6) released into the blood was evaluated.

Adjustment of Test Compound Solution. DMSO, polyethylene glycol #400, and 30% (w/v) hydroxypropyl-β-cyclodextrin were added to the test compounds in order and mixed well (solvent composition of 5:20:75) to adjust test compound solutions. For the solvent administration group, a solution of the similar solvent compositional feature without the test compounds was used.

CMA Stimulus Response. The test compound solutions adjusted to the solvent or test dose were orally administered to C57BL/6N mice (female, 7- to 8-week old) (4 mice per group). One hour after administration, CMA (manufactured by Tokyo Chemical Industry Co., Ltd.) suspended in 0.5% methylcellulose solution was administered intraperitoneally to the mice at a dose of 224 mg/kg. After 2 hours of CMA administration, blood samples were taken from each mouse, and the concentration of IFN-β and IL-6 in plasma was measured using Duoset ELISA Kit (manufactured by R&D systems).

Figure 2:
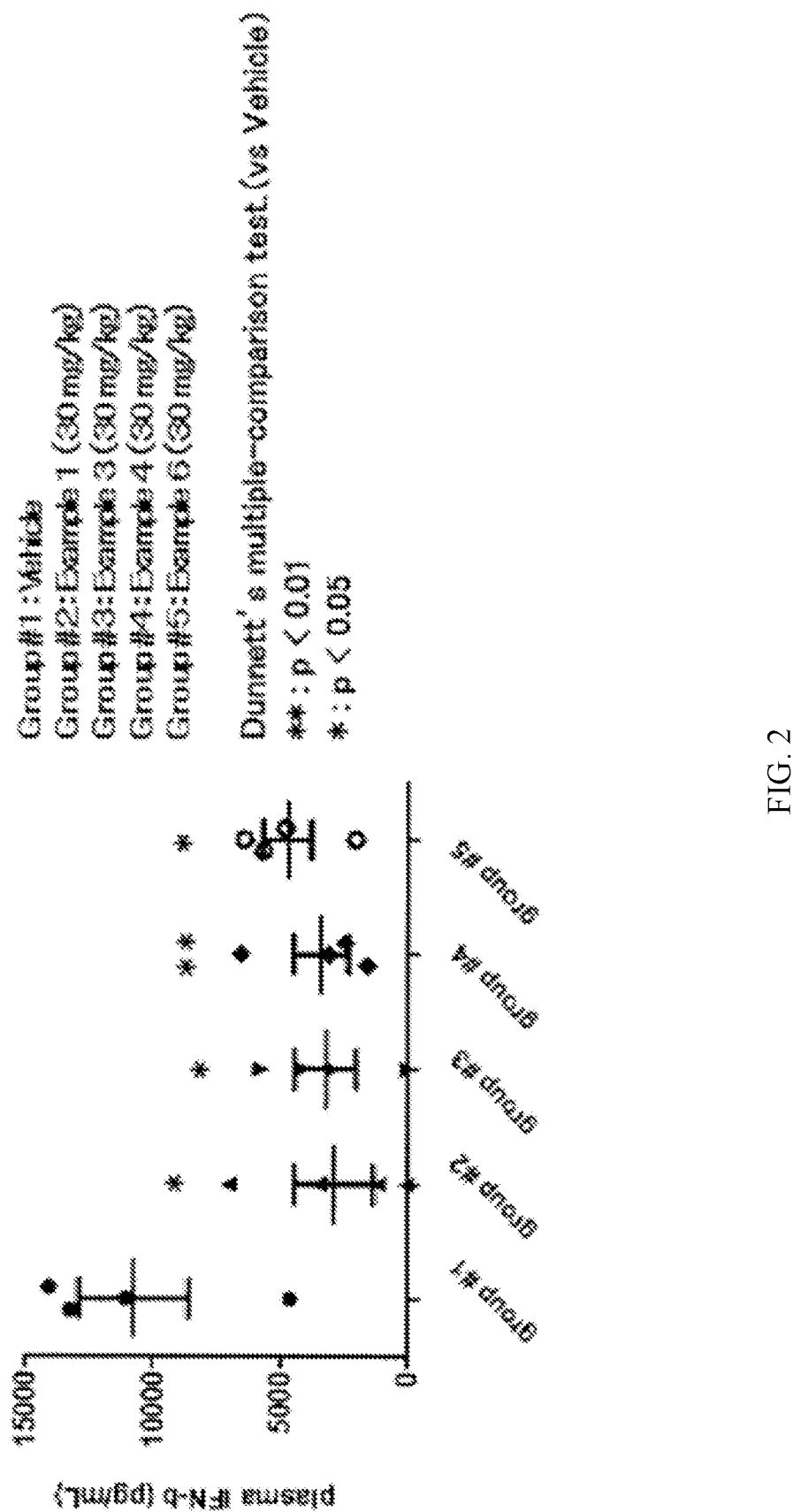
FIG. 2 shows a suppressing effect of a representative compound of Example on IFN-β production for STING agonist-stimulated mouse models (Test Example 3).

Evaluation Result. The results are shown in FIGS. 1 and 2. As shown in FIGS. 1 and 2, compared to the solvent group, representative compounds of the present invention significantly suppressed or tended to suppress the production of cytokines by STING stimulation. These results indicate that the compounds of formula (I) of the present invention has a suppressing effect on the production of IFN-β and IL-6 induced by the activation of STING in mice in vivo.

The compounds provided by the present invention are useful as a preventive or therapeutic pharmaceutical (pharmaceutical composition) for diseases known to be associated with STING-mediated cellular responses, such as inflammatory diseases, autoimmune diseases, or cancer. When combined with therapeutic agents for other inflammatory diseases, autoimmune diseases, and cancer, the compounds are expected to have an effect on immune responses and thus are also useful as a therapeutic pharmaceutical (pharmaceutical composition). As a STING inhibitor, they are further useful as a reagent for experiments and research.

While we have described a number of embodiments of this invention, it is apparent that our basic examples may be altered to provide other embodiments that utilize the compounds and methods of this invention. Therefore, the scope of this invention is to be defined by the appended claims rather than by the specific embodiments that have been represented by way of example.

CITATION LIST

[Non Patent Literature 1] Paludan, S. R. and Bowie, A. G., Immunity, 2013, 38(5), 870-880
[Non Patent Literature 2] Motwani M., et al., Nat. Rev. Genet., 2019, 20(11), 657-674
[Non Patent Literature 3] Liu, Y. et al., N. Engl. J. Med., 2014, 371(6), 507-518
[Non Patent Literature 4] Jeremiah, N., et al., J. Clin. Invest., 2014, 124(12), 5516-5520
[Non Patent Literature 5] Mackenzie, K. J., et al., ENBO J., 2016, 35(8), 831-844
[Non Patent Literature 6] An, J., et al., Arthritis Rheumatol., 2017, 69(4), 800-807
[Non Patent Literature 7] Kato, Y., et al., Ann. Rheum. Dis., 2018, 77(10), 1507-1515
[Non Patent Literature 8] Zeng, L., et al., Sci. Transl. Med., 2017, 9(412)
[Non Patent Literature 9] Hu, Q., et al., EBioMedicine, 2019, 41, 497-508
[Non Patent Literature 10] Yu, Y., et al., J. Clin. Invest., 2019, 129(2), 546-555
[Non Patent Literature 11] Iracheta-Vellve, A., et al., J. Biol. Chem., 2016, 291(52), 26794-26805
[Non Patent Literature 12] Maekawa, H., et al., Cell Rep., 2019, 29(5), 1261-1273. e6
[Non Patent Literature 13] Ahn, J., et al., Proc. Natl. Acad. Sci. U.S.A. 2012, 109(47), 19386-19391
[Non Patent Literature 14] Andrea, A. and Chen, Z. J., Science, 2019, 363(6431)
[Non Patent Literature 15] Sliter, D. A., et al., Nature, 2018, 561(7722), 258-262
[Non Patent Literature 16] Skopelja-Gardner S., et al., Nat. Rev. Nephrol., 2022 Jun. 22:1-5

The invention claimed is:

1. A compound of formula (I):

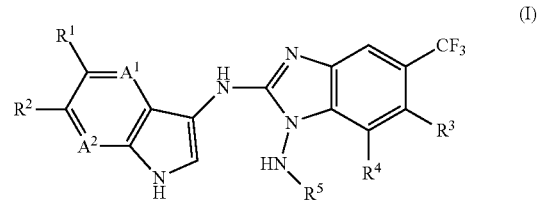

or a pharmaceutically acceptable salt thereof, wherein:
A1¹ represents a nitrogen atom or C-R⁶;
A² represents a nitrogen atom or C-R⁷;
R¹ represents a halogen atom or an alkyl group;
each of R², R³, R⁴, R⁶, and R⁷ independently represents a hydrogen atom or a fluorine atom, and R⁵ represents a hydrogen atom or an optionally substituted alkyl group.

2. The compound of claim 1, wherein A¹ and A² are represented by C-R⁶ and C-R⁷.

3. The compound of claim 1, wherein A¹ and A² are represented by a nitrogen atom and C-R⁷.

4. The compound of claim 1, wherein A¹ and A² are represented by C-R⁶ and a nitrogen atom.

5. The compound of claim 1, wherein R¹ is represented by a halogen atom.

6. The compound of claim 1, wherein the compound is a compound of formula (I-a):

(I-a)

[Structure]

or a pharmaceutically acceptable salt thereof, wherein:
A¹ represents a nitrogen atom or C-R⁶;
A² represents a nitrogen atom or C-R⁷;
R¹ represents a halogen atom or an alkyl group; and
each of R², R³, R⁶ and R⁷ independently represents a hydrogen atom or a fluorine atom.

7. The compound of claim 6, wherein A¹ and A² are represented by C-R⁶ and C-R⁷.

8. The compound of claim 6, wherein A¹ is represented by a nitrogen atom; and A² is represented by C-R⁷.

9. The compound of claim 6, wherein A¹ is represented by C-R⁶; and A² is represented by a nitrogen atom.

10. The compound of claim 6, wherein A¹ and A² are each represented by C-R⁶ and C-R⁷; and R⁶ and R⁷ are represented by a halogen atom.

11. The compound of claim 6, wherein A¹ and A² are each represented by C-R⁶ and C-R⁷; and R⁶ and R⁷ are each represented by hydrogen.

12. The compound of claim 6, wherein A¹ and A² are each represented by C-R⁶ and C-R⁷; R², R⁶ R⁷ are each represented by hydrogen; and R¹ is represented by a halogen atom.

13. The compound of claim 6, wherein A¹ and A¹ are each represented by C-R⁶ and C-R⁷; R⁶ and R⁷ are each represented by hydrogen; and R¹ is represented by a halogen atom.

14. The compound of claim 6, wherein A¹ and A² are each represented by C-R⁶ and C-R⁷; R², R⁶ and R⁷ are each represented by hydrogen; and R¹ is represented by a halogen atom.

15. The compound of claim 6, wherein A¹ and A² are each represented by C-R⁶ and C-R⁷; R², R³, R⁶ and R⁷ are each represented by hydrogen; and R¹ is represented by a halogen atom.

16. The compound of claim 1, wherein said compound is selected from:

-continued
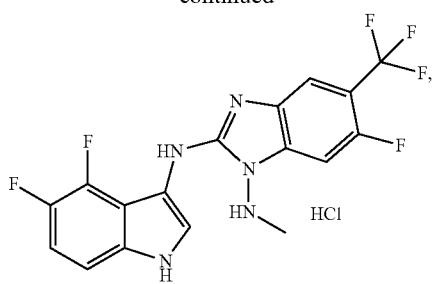
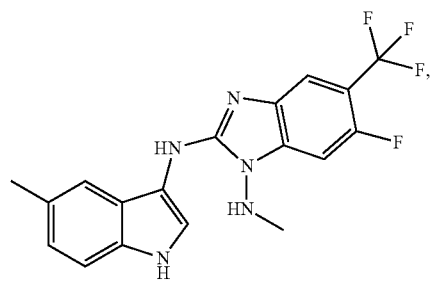
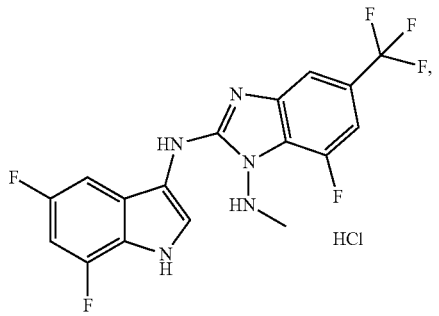
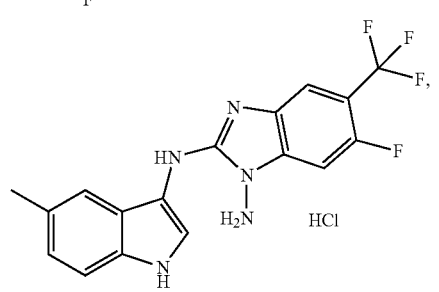
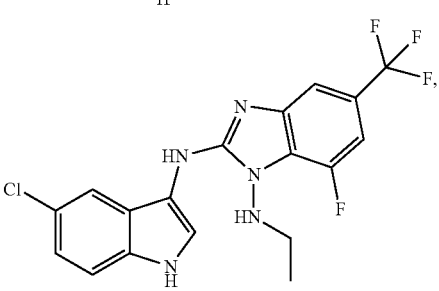
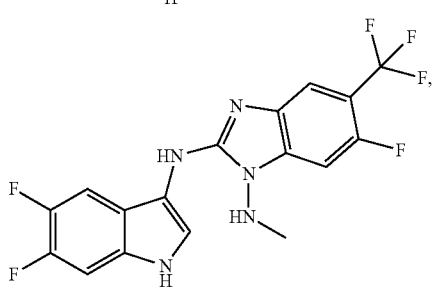
-continued
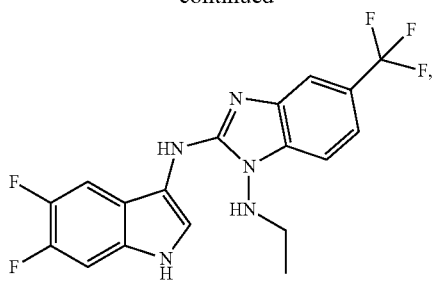
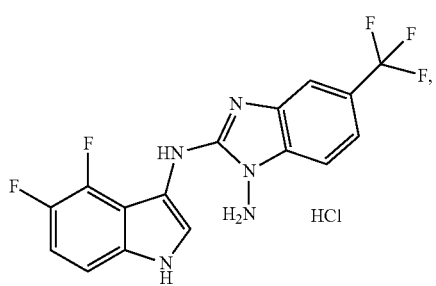
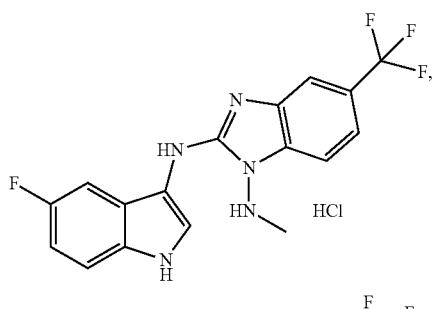
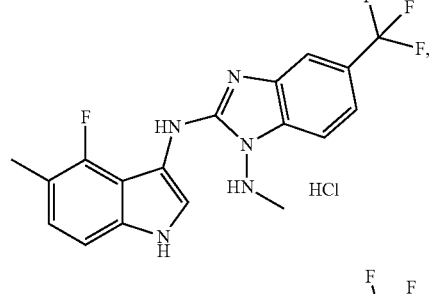
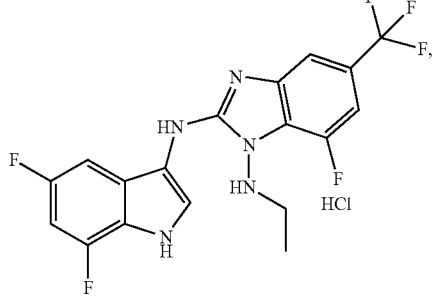
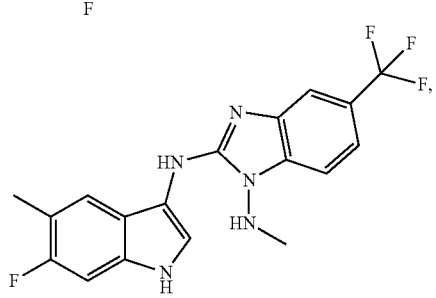

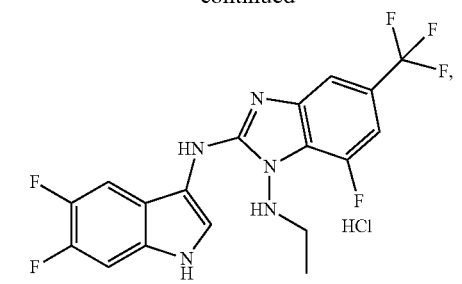
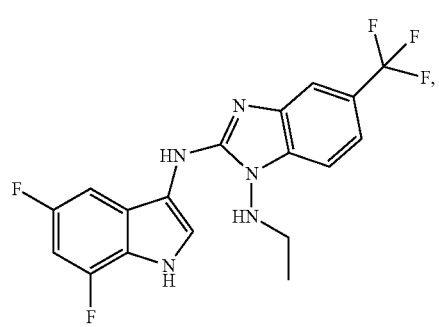
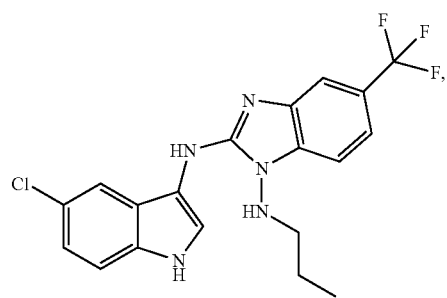
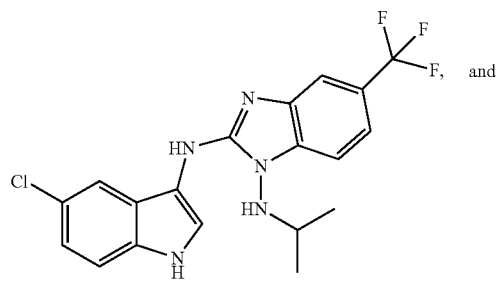 and
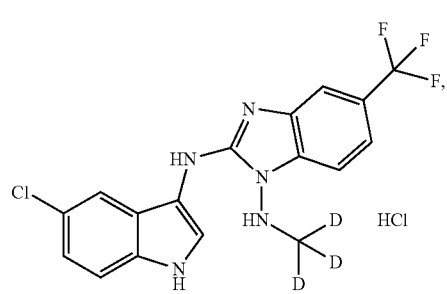
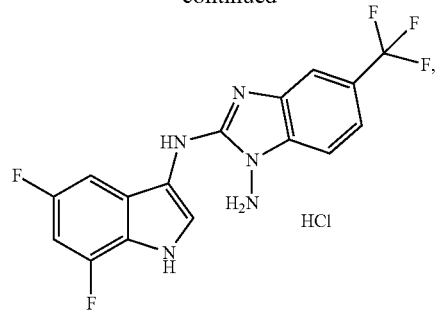
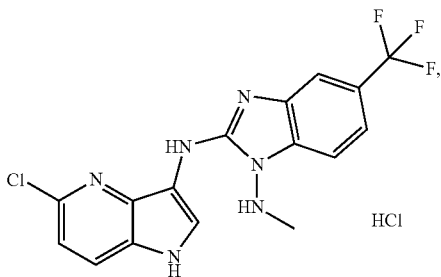
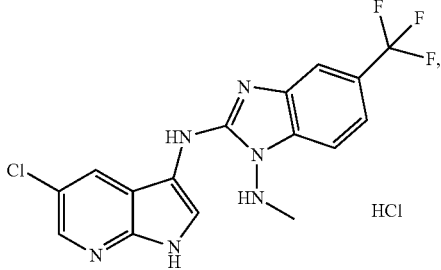
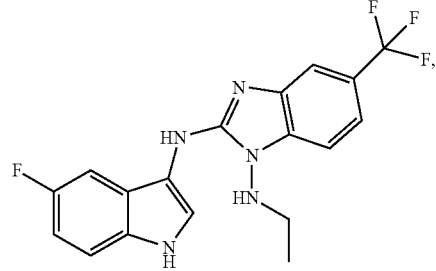
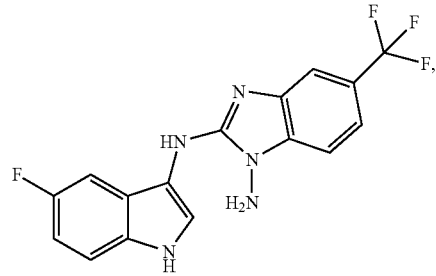
or a pharmaceutically acceptable salt thereof.
17. A pharmaceutical composition comprising a compound of claim 1 and a pharmaceutical carrier, isotonic agent, stabilizer, or preservative.
* * * * *